US007569646B1

(12) United States Patent
Canich

(10) Patent No.: US 7,569,646 B1
(45) Date of Patent: Aug. 4, 2009

(54) GROUP IVB TRANSITION METAL COMPOUNDS

(75) Inventor: Jo Ann Marie Canich, Webster, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 07/728,428

(22) Filed: Jul. 11, 1991

Related U.S. Application Data

(60) Division of application No. 07/533,245, filed on Jun. 4, 1990, now Pat. No. 5,055,438, which is a continuation-in-part of application No. 07/406,945, filed on Sep. 13, 1989, now abandoned.

(51) Int. Cl.
*C08F 4/642* (2006.01)
*C08F 4/6592* (2006.01)
*C07F 17/00* (2006.01)
*C07F 7/00* (2006.01)
*C07F 7/28* (2006.01)

(52) U.S. Cl. ........................ 526/160; 526/161; 526/170; 526/172; 526/943; 526/127; 556/11; 556/52

(58) Field of Classification Search .................. 556/11, 556/52; 526/141, 160, 161, 127, 170, 172, 526/943; 502/117, 103, 152, 154, 155
See application file for complete search history.

(56) References Cited

U.S. PATENT DOCUMENTS 4,931,417 A * 6/1990 Miya et al. .................... 556/11
5,045,517 A * 9/1991 Campbell et al. ........... 502/103
5,064,802 A * 11/1991 Stevens et al. ................ 556/11
5,276,117 A * 1/1994 Tomotsu et al. ............. 526/138
5,621,126 A * 4/1997 Canich et al. .................. 556/9
5,955,625 A * 9/1999 Canich .......................... 556/7
RE37,788 E * 7/2002 Canich .......................... 556/9
6,617,466 B1 * 9/2003 Canich ........................ 556/11
7,041,841 B1 * 5/2006 Canich ........................ 556/52
7,205,364 B1 * 4/2007 Canich ...................... 526/160

FOREIGN PATENT DOCUMENTS

WO A-87 03887 2/1987

OTHER PUBLICATIONS

"Gmelins Handbuch der Anorganischen Chemie", vol. 10; "Zirkonium-Organische Verbindungen", vol. 11; "Hafnium-Organische Verbindungen", 1973, Verlag Chemie, GmbH, Weinheim, DE "pp. 14-25, vol. 10; pp. 3-7, vol. 11".

Chemische Berichte, vol. 123, No. 8, Aug. 1990, pp. 1649-1651, Weinheim, DE: J. Okuda: "Synthesis and Complexation of Linked Cyclopentadienyl-Amido Ligands" "Whole document".

Organometallics, vol. 9, Sep. 1990, pp. 869-871, American Chemical Society, Washington, DC, US: P.J. Shapiro et al.: "[(N5-C5Me4)Me2Si(ni-NCMc3)(PMe3)(SeH]2: A Unique Example of a Single-Component Alpha-Olefin Polymerization Catalyst" Whole Document.

M. Reetz, *Organotitanium Reagents in Organic Synthesis*, pp. 117 and 121 (Springer-Verlay 1986.

Kukenhohner, "Untersuchungen zur Darstellung Chiraler Organotitan (IV)—Verbindungen fur *Enantioselektire Synthesen*" (1983) (unpublished Diplomarbeit, University of Marburg, Germany).

KukenHohner, Organotitan (IV) Agentien: Komplexe Chiraler Chelatliganden und *Enantioselektire c-c- Verknupfungen* (University of Marburg, Germany 1986).

* cited by examiner

*Primary Examiner*—Roberto Rábago

(57) ABSTRACT

The invention is a Group IVB transition metal compound which may be employed in the polymerization of olefins to produce high molecular weight polymers.

56 Claims, No Drawings

GROUP IVB TRANSITION METAL COMPOUNDS

This application is a division of Ser. No. 07/533,245, filed Jun. 4, 1990, now U.S. Pat. No. 5,055,438, which is a continuation-in-part of Ser. No. 07/406,945, filed Sep. 13, 1989, now abandoned.

FIELD OF THE INVENTION

This invention relates to certain transition metal compounds from Group IV B of the Periodic Table of Elements, to a catalyst system comprising a Group IV B transition metal compound and an alumoxane, and to a process using such catalyst system for the production of polyolefins, particularly polyethylene, polypropylene and α-olefin copolymers of ethylene and propylene having a high molecular weight. The catalyst system is highly active at low ratios of aluminum to the Group IV B transition metal, hence catalyzes the production of a polyolefin product containing low levels of catalyst residue.

BACKGROUND OF THE INVENTION

As is well known, various processes and catalysts exist for the homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin or an ethylene-α-olefin copolymer with high strength properties.

Traditional Ziegler-Natta catalyst systems—a transition metal compound cocatalyzed by an aluminum alkyl—are capable of producing polyolefins having a high molecular weight but a broad molecular weight distribution.

More recently a catalyst system has been developed wherein the transition metal compound has two or more cyclopentadienyl ring ligands, such transition metal compound being referred to as a metallocene—which catalyzes the production of olefin monomers to polyolefins. Accordingly, metallocene compounds of the Group IV B metals, particularly, titanocene and zirconocene, have been utilized as the transition metal component in such "metallocene" containing catalyst system for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity which catalyzes the production of polyolefins.

A wide variety of Group IV B transition metal compounds of the metallocene type have been named as possible candidates for an alumoxane cocatalyzed catalyst system. Hence, although bis(cyclopentadienyl) Group IV B transition metal compounds have been the most preferred and heavily investigated type metallocenes for use in metallocene/alumoxane catalyst for polyolefin production, suggestions have appeared that mono and tris(cyclopentadienyl) transition metal compounds may also be useful. See, for example, U.S. Pat. Nos. 4,522,982; 4,530,914 and 4,701,431. Such mono(cyclopentadienyl) transition metal compounds as have heretofore been suggested as candidates for a metallocene/alumoxane catalyst are mono(cyclopentadienyl) transition metal trihalides and trialkyls.

More recently International Publication No. WO 87/03887 has appeared which describes the use of a composition comprising a transition metal coordinated to at least one cyclopentadienyl and at least one heteroatom ligand as a metallocene type component for use in a metallocene/alumoxane catalyst system for α-olefin polymerization. The composition is broadly defined as a transition metal, preferably of Group IV B of the Periodic Table which is coordinated with at least one cyclopentadienyl ligand and one to three heteroatom ligands, the balance of the coordination requirement being satisfied with cyclopentadienyl or hydrocarbyl ligands. The metallocene/alumoxane catalyst system described is illustrated solely with reference to transition metal compounds which are bis(cyclopentadienyl) Group IV B transition metal compounds.

Even more recently, at the Third Chemical Congress of North America held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such transition metal compound could be usefully employed for commercial polymerization processes.

A need still exists for discovering catalyst systems that permit the production of higher molecular weight polyolefins and desirably with a narrow molecular weight distribution.

SUMMARY OF THE INVENTION

The catalyst system of this invention comprises a transition metal component from Group IV B of the Periodic Table of the Elements (*CRC Handbook of Chemistry and Physics*, 68th ed. 1987-1988) and an alumoxane component which may be employed in solution, slurry or bulk phase polymerization procedure to produce a polyolefin of high weight average molecular weight and relatively narrow molecular weight distribution.

The "Group IV B transition metal component" of the catalyst system is represented by the general formula:

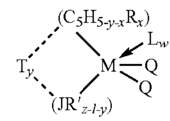

wherein: M is Zr, Hf or Ti and is in its highest formal oxidation state (+4, $d^0$ complex);

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the Group IV A of the Periodic Table of Elements, and halogen radicals or $(C_5H_{5-y-x}R_x)$ is a cyclopentadienyl ring in which two adjacent R-groups are joined forming $C_4$-$C_{20}$ ring to give a saturated or unsaturated polycyclic cyclopentadienyl ligand such as indenyl, tetrahydroindenyl, fluorenyl or octahydrofluorenyl;

($JR'_{z-1-y}$) is a heteroatom ligand in which J is an element with a coordination number of three from Group V A or an element with a coordination number of two from Group VI A of the Periodic Table of Elements, preferably nitrogen, phosphorus, oxygen or sulfur, and each R' is, independently a radical selected from a group consisting of $C_1$-$C_{20}$ hydrocarbyl radicals, substituted $C_1$-$C_{20}$ hydrocarbyl radicals wherein one or more hydrogen atoms is replaced by a halogen atom, and "z" is the coordination number of the element J;

each Q may be independently any univalent anionic ligand such as halogen, hydride, or substituted or unsubstituted $C_1$-$C_{20}$ hydrocarbyl, alkoxide, aryloxide, amide, arylamide, phosphide or arylphosphide, provided that where any Q is a hydrocarbyl such Q is different from ($C_5H_{5-y-x}R_x$), or both Q together may be an alkylidene or a cyclometallated hydrocarbyl or any other divalent anionic chelating ligand.

"y" is 0 or 1 when w is greater than 0; y is 1 when w is 0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

L is a Lewis base such as diethylether, tetraethylammonium chloride, tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q', wherein M' has the same meaning as M and Q' has the same meaning as Q. Such compounds are represented by the formula:

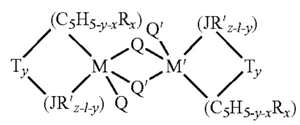

The alumoxane component of the catalyst may be represented by the formulas: $(R^2—Al—O)_m$; $R^3(R^4—Al—O)_m—AlR^5$ or mixtures thereof, wherein $R^2$-$R^5$ are, independently, a univalent anionic ligand such as a $C_1$-$C_5$ alkyl group or halide and "m" is an integer ranging from 1 to about 50 and preferably is from about 13 to about 25.

Catalyst systems of the invention may be prepared by placing the "Group IV B transition metal component" and the alumoxane component in common solution in a normally liquid alkane or aromatic solvent, which solvent is preferably suitable for use as a polymerization diluent for the liquid phase polymerization of an olefin monomer.

A typical polymerization process of the invention such as for the polymerization or copolymerization of olefins comprises the steps of contacting ethylene or $C_3$-$C_{20}$ α-olefins alone or with other unsaturated monomers including $C_3$-$C_{20}$ α-olefins, $C_5$-$C_{20}$ diolefins, and/or acetylenically unsaturated monomers either alone or in combination with other olefins and/or other unsaturated monomers, with a catalyst comprising, in a suitable polymerization diluent, the Group IV B transition metal component illustrated above; and a methylalumoxane in an amount to provide a molar aluminum to transition metal ratio of from about 1:1 to about 20,000:1 or more; and reacting such monomer in the presence of such catalyst system at a temperature of from about −100° C. to about 300° C. for a time of from about 1 second to about 10 hours to produce a polyolefin having a weight average molecular weight of from about 1,000 or less to about 5,000,000 or more and a molecular weight distribution of from about 1.5 to about 15.0.

DESCRIPTION OF THE PREFERRED EMBODIMENT

Catalyst Component

The Group IV B transition metal component of the catalyst system is represented by the general formula:

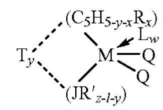

wherein: M is Zr, Hf or Ti and is in its highest formal oxidation state (+4, $d^0$ complex);

($C_5H_{5-y-x}R_x$) is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the Group IV A of the Periodic Table of Elements, and halogen radicals or ($C_5H_{5-y-x}R_x$) is a cyclopentadienyl ring in which two adjacent R-groups are joined forming $C_4$-$C_{20}$ ring to give a saturated or unsaturated polycyclic cyclopentadienyl ligand such as indenyl, tetrahydroindenyl, fluorenyl or octahydrofluorenyl;

($JR'_{z-1-y}$) is a heteroatom ligand in which J is an element with a coordination number of three from Group V A or an element with a coordination number of two from Group VI A of the Periodic Table of Elements, preferably nitrogen, phosphorus, oxygen or sulfur with nitrogen being preferred, and each R' is, independently a radical selected from a group consisting of $C_1$-$C_{20}$ hydrocarbyl radicals, substituted $C_1$-$C_{20}$ hydrocarbyl radicals wherein one or more hydrogen atoms is replaced by a halogen atom, and "z" is the coordination number of the element J;

each Q is, independently any univalent anionic ligand such as halogen, hydride, or substituted or unsubstituted $C_1$-$C_{20}$ hydrocarbyl, alkoxide, aryloxide, amide, arylamide, phosphide or arylphosphide, provided that where any Q is a hydrocarbyl such Q is different from ($C_5H_{5-y-x}R_x$), or both Q together may be an alkylidene or a cyclometallated hydrocarbyl or any other divalent anionic chelating ligand;

"y" is 0 or 1 when w is greater than 0, y is 1 when w=0; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like. L is defined as heretofore. Examples of the B group which are suitable as a constituent group of the Group IV B transition metal component of the catalyst system are identified in Column 1 of Table 1 under the heading "B".

Exemplary hydrocarbyl radicals for the Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for Q include chlorine, bromine, fluorine and iodine, with chlorine being preferred. Exemplary alkoxides and aryloxides for Q are methoxide, phenoxide and substituted phenoxides such as 4-methylphenoxide. Exemplary amides for Q are dimethylamide, diethylamide, methylethylamide, di-t-butylamide, diisopropylamide and the like. Exemplary aryl amides are diphenylamide and any other substituted phenyl amides. Exemplary phosphides for Q are diphenylphosphide, dicyclohexylphosphide, diethylphosphide, dimethylphosphide and the like. Exemplary alkylidene radicals for both Q together are methylidene, ethylidene and propylidene. Examples of the Q group which are suitable as a constituent group or element of the Group IV B transition metal component of the catalyst system are identified in Column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals, alkyl-substituted aromatic radicals and cyclopentadienyl rings containing 1 or more fused saturated or unsaturated rings. Suitable organometalloid radicals, which may be substituted as an R group for at least one hydrogen atom in the cyclopentadienyl ring, include trimethylsilyl, triethylsilyl, ethyldimethylsilyl, methyldiethylsilyl, triphenylgermyl, trimethylgermyl and the like. Examples of cyclopentadienyl ring groups ($C_5H_{5-y-x}R_x$) which are suitable as a constituent group of the Group IV B transition metal component of the catalyst system are identified in Column 2 of Table 1 under the heading ($C_5H_{5-y-x}R_x$).

Suitable hydrocarbyl and substituted hydrocarbyl radicals, which may be substituted as an R' group for at least one hydrogen atom in the heteroatom J ligand group, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Examples of heteroatom ligand groups ($JR'_{z-1-y}$) which are suitable as a constituent group of the Group IV B transition metal component of the catalyst system are identified in Column 3 of Table 1 under the heading ($JR'_{z-1-y}$).

Table 1 depicts representative constituent moieties for the "Group IV B transition metal component", the list is for illustrative purposes only and should not be construed to be limiting in any way. A number of final components may be formed by permuting all possible combinations of the constituent moieties with each other. Illustrative compounds are: dimethylsilyltetramethylcyclopentadienyl-tert-butylamido zirconium dichloride, dimethylsilyltetramethylcyclopentadienyl-tert-butylamido hafnium dichloride, dimethylsilyl-tert-butylcyclopentadienyl-tert-butylamido zirconium dichloride, dimethylsilyl-tert-butylcyclopentadienyl-tert-butylamido hafnium dichloride, dimethylsilyltrimethylsilylcyclopentadienyl-tert-butylamido zirconium dichloride, dimethylsilyltetramethylcyclopentadienylphenylamido zirconium dichloride, dimethylsilyltetramethylcyclopentadienylphenylamido hafnium dichloride, methylphenylsilyltetramethylcyclopentadienyl-tert-butylamido zirconium dichloride, methylphenylsilyltetramethylcyclopentadienyl-tert-butylamido hafnium dichloride, methylphenylsilyltetramethylcyclopentadienyl-tert-butylamido hafnium dimethyl, dimethylsilyltetramethylcyclopentadienyl-p-n-butylphenylamido zirconium dichloride, dimethylsilyltetramethylcyclopentadienyl-p-n-butylphenylamido hafnium dichloride. For illustrative purposes, the above compounds and those permuted from Table 1 does not include the Lewis base ligand (L). The conditions under which complexes containing Lewis base ligands such as ether or those which form dimers is determined by the steric bulk of the ligands about the metal center. For example, the t-butyl group in $Me_2Si(Me_4C_5)(N\text{-}t\text{-}Bu)ZrCl_2$ has greater steric requirements than the phenyl group in $Me_2Si(Me_4C_5)(NPh)ZrCl_2.Et_2O$ thereby not permitting ether coordination in the former compound. Similarly, due to the decreased steric bulk of the trimethylsilylcyclopentadienyl group in $[Me_2Si(Me_3SiC_5H_3)(N\text{-}t\text{-}Bu)ZrCl_2]_2$ versus that of the tetramethylcyclopentadienyl group in $Me_2Si(Me_4C_5)(N\text{-}t\text{-}Bu)ZrCl_2$, the former compound is dimeric and the latter is not.

TABLE 1

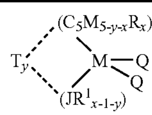

| T (when y = 1) | ($C_5M_{5-y-x}R_x$) | ($JR'_{z-1-y}$) | Q | M |
|---|---|---|---|---|
| dimethylsilyl | cyclopentadienyl | t-butylamido | hydride | zirconium |
| diethylysilyl | methylcyclopentadienyl | phenylamido | chloro | hafnium |
| di-n-propylsilyl | 1,2-dimethylcyclopentadienyl | p-n-butylphenylamido | methyl | titanium |
| diisopropylsilyl | 1,3-dimethylcyclopentadienyl | cyclohexylamido | ethyl | |
| di-n-butylsilyl | indenyl | perflurophenylamido | phenyl | |
| di-t-butylsilyl | 1,2-diethylcyclopentadienyl | n-butylamido | fluoro | |
| di-n-hexylsilyl | tetramethylcyclopentadienyl | methylamido | bromo | |
| methylphenylsilyl | ethylcyclopentadienyl | ethylamido | iodo | |
| ethylmethylsilyl | n-butylcyclopentadienyl | n-propylamido | n-propyl | |
| diphenylsilyl | cyclohexylmethylcyclopentadienyl | isopropylamido | isopropyl | |
| di(p-t-butylphenethylsilyl) | n-octylcyclopentadienyl | benzylamido | n-butyl | |
| n-hexylmethylsilyl | β-phenylpropylcyclopentadienyl | i-butylphospheido | amyl | |
| cyclopentamethylenesilyl | tetrahydroindenyl | ethylphosphido | isoamyl | |
| cyclotetramethylenesilyl | propylcyclopentadienyl | phenylphosphido | hexyl | |
| cyclotrimethylenesilyl | t-butylcyclopentadienyl | cyclohexylphosphido | isobutyl | |

TABLE 1-continued

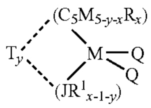

| T (when y = 1) | $(C_5M_{5\text{-}y\text{-}x}R_{x})$ | $(JR'_{z\text{-}1\text{-}y})$ | Q | M |
|---|---|---|---|---|
| dimethylgermanyl | benzylcyclopentadienyl | oxo (when y = 1) | heptyl | |
| diethylgermanyl | diphenylmethylcyclopentadienyl | sulfido (when y = 1) | octyl | |
| phenylamido | trimethylgermylcyclopentadienyl | methoxide (when y = 0) | nonyl | |
| t-butylamido | trimethylstannylcyclopentadienyl | ethoxide (when y = 0) | decyl | |
| methylamido | triethylplumbylcyclopentadienyl | methylthio (when y = 0) | cetyl | |
| i-butylphosphido | trifluromethylcyclopentadienyl | ethylthio (when y = 0) | methoxy | |
| ethylphosphido | trimethylsilylcyclopentadienyl | | ethoxy | |
| phenylphosphido | pentamethylcycloopentadienyl (when y = 0) | | propoxy | |
| methylene | fluorenyl | | butoxy | |
| dimethylmethylene | octahydrofluorenyl | | phenoxy | |
| diethylmethylene | | | dimethylamido | |
| ethylene | | | diethylamido | |
| dimethylethylene | | | methylethylamido | |
| diethylethylene | | | di-i-butylamido | |
| dipropylethylene | | | diphenylamido | |
| propylene | | | diphenylphosphido | |
| dimethylpropylene | | | dicyclohexylphosphido | |
| diethylpropylene | | | dimethylphosphido | |
| 1,1-dimethyl-3,3,-dimethylpropylene | | | methylidene (both Q) | |
| tetramethyldisilexene | | | ethylidene (both Q) | |
| 1,1,4,4-tetramethylidisilylethylene | | | propylidene (both Q) | |
| | | | ethyleneglycol dianion | |

Generally the bridged species of the Group IV B transition metal compound ("y"=1) are preferred. These compounds can be prepared by reacting a cyclopentadienyl lithium compound with a dihalo compound whereupon a lithium halide salt is liberated and a monohalo substituent becomes covalently bound to the cyclopentadienyl compound. The so substituted cyclopentadienyl reaction product is next reacted with a lithium salt of a phosphide, oxide, sulfide or amide (for the sake of illustrative purposes, a lithium amide) whereupon the halo element of the monohalo substituent group of the reaction product reacts to liberate a lithium halide salt and the amine moiety of the lithium amide salt becomes covalently bound to the substituent of the cyclopentadienyl reaction product. The resulting amine derivative of the cyclopentadienyl product is then reacted with an alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide.

Unbridged species of the Group IV B transition metal compound can be prepared from the reaction of a cyclopentadienyl lithium compound and a lithium salt of an amine with a Group IV B transition metal halide.

Suitable, but not limiting, Group IV B transition metal compounds which may be utilized in the catalyst system of this invention include those bridged species ("y"=1) wherein the B group bridge is a dialkyl, diaryl or alkylaryl silane, or methylene or ethylene. Exemplary of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Suitable Group IV B transition metal compounds which are illustrative of the unbridged ("y"=0) species which may be utilized in the catalyst systems of this invention are exemplified by pentamethylcyclopentadienyldi-t-butylphosphinodimethyl hafnium; pentamethylcyclopentadienyldi-t-butylphosphinomethylethyl hafnium; cyclopentadienyl-2-methylbutoxide dimethyl titanium.

To illustrate members of the Group IV B transition metal component, select any combination of the species in Table 1. An example of a bridged species would be dimethylsilylcyclopentadienyl-t-butylamidodichloro zirconium; an example of an unbridged species would be cyclopentadienyldi-t-butylamidodichloro zirconium.

The alumoxane component of the catalyst system is an oligomeric compound which may be represented by the general formula $(R^2—Al—O)_m$ which is a cyclic compound, or may be $R^3(R^4—Al—O—)_m—AlR_2^5$ which is a linear compound. An alumoxane is generally a mixture of both the linear and cyclic compounds. In the general alumoxane formula $R^2$, $R^3$, $R^4$, and $R^5$ are, independently a univalent anionic ligand such as a $C_1$-$C_5$ alkyl radical, for example, methyl, ethyl, propyl, butyl, pentyl or halide and "m" is an integer from 1 to about 50. Most preferably, $R^2$, $R^3$, $R^4$ and $R^5$ are each methyl and "m" is at least 4. When an alkyl aluminum halide is employed in the preparation of alumoxane, one or more of $R^{2-5}$ could be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both the linear and cyclic species of alumoxane.

Suitable alumoxanes which may be utilized in the catalyst systems of this invention are those prepared by the hydrolysis of a alkylaluminum reagent; such as trimethylaluminum, triethylaluminum, tripropylaluminum; triisobutylaluminum, dimethylaluminumchloride, diisobutylaluminumchloride, diethylaluminumchloride, and the like. The most preferred alumoxane for use is methylalumoxane (MAO), particularly methylalumoxanes having a reported average degree of oligomerization of from about 4 to about 25 ("m"=4 to 25) with a range of 13 to 25 being most preferred.

Catalyst Systems

The catalyst systems employed in the method of the invention comprise a complex formed upon admixture of the Group IV B transition metal component with an alumoxane component. The catalyst system may be prepared by addition of the requisite Group IV B transition metal and alumoxane components to an inert solvent in which olefin polymerization can be carried out by a solution, slurry or bulk phase polymerization procedure.

The catalyst system may be conveniently prepared by placing the selected Group IV B transition metal component and the selected alumoxane component, in any order of addition, in an alkane or aromatic hydrocarbon solvent—preferably one which is also suitable for service as a polymerization diluent. Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

In accordance with this invention optimum results are generally obtained wherein the Group IV B transition metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1. Sufficient solvent should be employed so as to provide adequate heat transfer away from the catalyst components during reaction and to permit good mixing.

The catalyst system ingredients—that is, the Group IV B transition metal, the alumoxane, and polymerization diluent can be added to the reaction vessel rapidly or slowly. The temperature maintained during the contact of the catalyst components can vary widely, such as, for example, from −10° to 300° C. Greater or lesser temperatures can also be employed. Preferably, during formation of the catalyst system, the reaction is maintained within a temperature of from about 25° to 100° C., most preferably about 25° C.

At all times, the individual catalyst system components, as well as the catalyst system once formed, are protected from oxygen and moisture. Therefore, the reactions are performed in an oxygen and moisture free atmosphere and, where the catalyst system is recovered separately it is recovered in an oxygen and moisture free atmosphere. Preferably, therefore, the reactions are performed in the presence of an inert dry gas such as, for example, helium or nitrogen.

Polymerization Process

In a preferred embodiment of the process of this invention the catalyst system is utilized in liquid phase (slurry, solution, suspension or bulk phase and combination thereof), high pressure fluid phase or gas phase polymerization of an olefin monomer. These processes may be employed singularly or in series. The liquid phase process comprises the steps of contacting an olefin monomer with the catalyst system in a suitable polymerization diluent and reacting said monomer in the presence of said catalyst system for a time and at a temperature sufficient to produce a polyolefin or high molecular weight.

The monomer for such process may comprise ethylene alone, for the production of a homopolyethylene, or ethylene in combination with an α-olefin having 3 to 20 carbon atoms for the production of an ethylene-α-olefin copolymer. Homopolymers of higher α-olefin such as propylene, butene, styrene and copolymers thereof with ethylene and/or $C_4$ or higher α-olefins and diolefins can also be prepared. Conditions most preferred for the homo- or co-polymerization of ethylene are those wherein ethylene is submitted to the reaction zone at pressures of from about 0.019 psia to about 50,000 psia and the reaction temperature is maintained at from about −100° to about 300° C. The aluminum to transition metal molar ratio is preferably from about 1:1 to 18,000 to 1. A preferable range would be 1:1 to 1000:1. The reaction time is preferably from about 1 min to about 1 hr. Without limiting in any way the scope of the invention, one means for carrying out the process of the present invention is as follows: in a stirred-tank reactor liquid 1-butene monomer is introduced. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid 1-butene together with dissolved ethylene gas, and a vapor phase containing vapors of all monomers. The reactor temperature and pressure may be controlled via reflux of vaporizing α-olefin monomer (autorefrigeration), as well as by cooling coils, jackets etc. The polymerization rate is controlled by the concentration of catalyst. The ethylene content of the polymer product is determined by the ratio of ethylene to 1-butene in the reactor, which is controlled by manipulating the relative feed rates of these components to the reactor.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used. This technique is discussed in "Liquid Chromatography of Polymers and Related Materials III", J. Cazes editor, Marcel Dekker, 1981, p. 207 which is incorporated herein by reference. No corrections for column spreading were employed; however, data on generally accepted standards, e.g. National Bureau of Standards Polyethylene 1484 and anionically produced hydrogenated polyisoprenes (an alternating ethylene-propylene copolymer) demonstrated that such corrections on Mw/Mn (=MWD) were less than 0.05 units. Mw/Mn was calculated from elution times. The numerical analyses were performed using the commercially available Beckman/CIS customized LALLS software in conjunction with the standard Gel Permeation package, run on a HP 1000 computer.

The following examples are intended to illustrate specific embodiments of the invention and are not intended to limit the scope of the invention.

All procedures were performed under an inert atmosphere of helium or nitrogen. Solvent choices are often optional, for example, in most cases either pentane or 30-60 petroleum ether can be interchanged. The lithiated amides were prepared from the corresponding amines and either n-BuLi or MeLi. Published methods for preparing $LiHC_5Me_4$ include C. M. Fendrick et al. *Organometallics*, 3, 819 (1984) and F. H. Köhler and K. H. Doll. *Z. Naturforsch*, 376, 144 (1982). Other lithiated substituted cyclopentadienyl compounds are typically prepared from the corresponding cyclopentadienyl ligand and n-BuLi or MeLi, or by reaction of MeLi with the proper fulvene. $ZrCl_4$ and $HfCl_4$ were purchased from either Aldrich Chemical Company or Cerac. Amines, silanes and lithium reagents were purchased from Aldrich Chemical Company or Petrarch Systems. Methylalumoxane was supplied by either Sherring or Ethyl Corp.

Examples A-L of Group IV B Transition Metal Components

Example A

Compound A: Part 1. $Me_4HC_5Li$ (10.0 g, 0.078 mol) was slowly added to a $Me_2SiCl_2$ (11.5 ml, 0.095 mol, in 225 ml of tetrahydrofuran (thf) solution). The solution was stirred for 1 hour to assure complete reaction. The thf solvent was then removed via a vacuum to a cold trap held at −196° C. Pentane was added to precipitate out the LiCl. The mixture was filtered through Celite. The solvent was removed from the filtrate. $Me_4HC_5SiMe_2Cl$ (15.34 g, 0.071 mol) was recovered as a pale yellow liquid.

Part 2. $Me_4HC_5SiMe_2Cl$ (10.0 g, 0.047 mol) was slowly added to a suspension of LiHN-t-Bu (3.68 g, 0.047 mol, ~100 ml thf). The mixture was stirred overnight. The thf was then removed via a vacuum to a cold trap held at −196° C. Petroleum ether (~100 ml) was added to precipitate out the LiCl. The mixture was filtered through Celite. The solvent was removed from the filtrate. $Me_2Si(Me_4HC_5)$(HN-t-Bu) (11.14 g, 0.044 mol) was isolated as a pale yellow liquid.

Part 3. $Me_2Si(Me_4HC_5)$(HN-t-Bu) (11.14 g, 0.044 mol) was diluted with ~100 ml $Et_2O$. MeLi (1.4 M, 64 ml, 0.090 mol) was slowly added. The mixture was allowed to stir for ½ hour after the final addition of MeLi. The ether was reduced in volume prior to filtering off the product. The product, $[Me_2Si(Me_4C_5)$(N-t-Bu)$]Li_2$, was washed with several small portions of ether, then vacuum dried.

Part 4. $[Me_2Si(Me_4C_5)$(N-t-Bu)$]Li_2$ (3.0 g, 0.011 mol) was suspended in ~150 ml $Et_2O$. $ZrCl_4$ (2.65 g, 0.011 mol) was slowly added and the resulting mixture was allowed to stir overnight. The ether was removed via a vacuum to a cold trap held at −196° C. Pentane was added to precipitate out the LiCl. The mixture was filtered through Celite twice. The pentane was significantly reduced in volume and the pale yellow solid was filtered off and washed with solvent. $Me_2Si(Me_4C_5)$(N-t-Bu)$ZrCl_2$ (1.07 g, 0.0026 mole) was recovered. Additional $Me_2Si(Me_4C_5)$(N-t-Bu)$ZrCl_2$ was recovered from the filtrate by repeating the recrystallization procedure. Total yield, 1.94 g, 0.0047 mol).

Example B

Compound B: The same procedure of Example A for preparing compound A was followed with the exception of the use of $HfCl_4$ in place of $ZrCl_4$ in Part 4. Thus, when $[Me_2Si(Me_4C_5)$(N-t-Bu)$]Li_2$ (2.13 g, 0.0081 mol) and $HfCl_4$ (2.59 g, 0.0081 mol) were used. $Me_2Si(Me_4C_5)$(N-t-Bu)$HfCl_2$ (0.98 g, 0.0020 mol) was produced.

Example C

Compound C: Part 1. $Me_2SiCl_2$ (7.5 ml, 0.062 mol) was diluted with ~30 ml thf. A t-$BuH_4C_5Li$ solution (7.29 g, 0.056 mol, ~100 ml thf) was slowly added, and the resulting mixture was allowed to stir overnight. The thf was removed via a vacuum to a trap held at −196° C. Pentane was added to precipitate out the LiCl, and the mixture was filtered through Celite. The pentane was removed from the filtrate leaving behind a pale yellow liquid, t-$BuH_4C_5SiMe_2Cl$ (10.4 g, 0.048 mol).

Part 2. To a thf solution of LiHN-t-Bu (3.83 g, 0.048 mol, ~125 ml), t-$BuH_4C_5SiMe_2Cl$ (10.4 g, 0.048 mol) was added drop wise. The resulting solution was allowed to stir overnight. The thf was removed via a vacuum to a trap held at −196° C. Pentane was added to precipitate out the LiCl, and the mixture was filtered through Celite. The pentane was removed from the filtrate leaving behind a pale yellow liquid, $Me_2Si$(t-$BuH_4C_5$)(NH-t-Bu) (11.4 g, 0.045 mol).

Part 3. $Me_2Si$(t-$BuH_4C_5$)(NH-t-Bu) (11.4 g, 0.045 mol) was diluted with ~100 ml $Et_2O$. MeLi (1.4 M, 70 ml, 0.098 mol) was slowly added. The mixture was allowed to stir overnight. The ether was removed via a vacuum to a trap held at −196° C., leaving behind a pale yellow solid, $[Me_2Si$(t-$BuH_3C_5$)(N-t-Bu)$]Li_2$ (11.9 g, 0.045 mol).

Part 4. $[Me_2Si$(t-$BuH_3C_5$)(N-t-Bu)$]Li_2$ (3.39 g, 0.013 mol) was suspended in ~100 ml $Et_2O$. $ZrCl_4$ (3.0 g, 0.013 mol) was slowly added. The mixture was allowed to stir overnight. The ether was removed and pentane was added to precipitate out the LiCl. The mixture was filtered through Celite. The pentane solution was reduced in volume, and the pale tan solid was filtered off and washed several times with small quantities of pentane. The product of empirical formula $Me_2Si$(t-$BuH_3C_5$)(N-t-Bu)$ZrCl_2$ (2.43 g, 0.0059 mol) was isolated.

Example D

Compound D: The same procedure of Example C for preparing compound C was followed with the exception of the use of $HfCl_4$ in Part 4. Thus, when $[Me_2Si$(t-$BuH_3C_5$)(N-t-Bu)$]Li_2$ (3.29 g, 0.012 mol) and $HfCl_4$ (4.0 g, 0.012 mol) were used, the product of the empirical formula $Me_2Si(t\text{-}BuH_3C_5)(N\text{-}t\text{-}Bu)HfCl_2$ (1.86 g, 0.0037 mol) was produced.

Example E

Compound E. Part 1. $Me_2SiCl_2$ (7.0 g, 0.054 mol) was diluted with ~100 ml of ether. $Me_3SiC_5H_4Li$ (5.9 g, 0.041 mol) was slowly added. Approximately 75 ml of thf was added and the mixture was allowed to stir overnight. The solvent was removed via a vacuum to a cold trap held at −196° C. Pentane was added to precipitate out the LiCl. The mixture was filtered through Celite. The solvent was removed from the filtrate giving $Me_2Si(Me_3SiC_5H_4)Cl$ (8.1 g, 0.035 mol) as a pale yellow liquid.

Part 2. $Me_2Si(Me_3SiC_5H_4)Cl$ (3.96 g, 0.017 mol) was diluted with ~50 ml of ether. LiHN-t-Bu (1.36 g, 0.017 mol) was slowly added, and the mixture was allowed to stir overnight. The ether was removed via a vacuum and pentane was added to precipitate the LiCl. The mixture was filtered through Celite, and the pentane was removed from the filtrate. $Me_2Si(Me_3SiC_5H_4)(NH\text{-}t\text{-}Bu)$ (3.7 g, 0.014 mol) was isolated as a pale yellow liquid.

Part 3. $Me_2Si(Me_3SiC_5H_4)(NH\text{-}t\text{-}Bu)$ (3.7 g, 0.014 mol) as diluted with ether. MeLi (25 ml, 1.4M in ether, 0.035 mol) was slowly added. The mixture was allowed to stir for 1.5 hours after the final addition of MeLi. The ether was removed via vacuum producing 4.6 g of a white solid formulated as $Li_2[Me_2Si(Me_3SiC_5H_3)(N\text{-}t\text{-}Bu)].¾Et_2O$ and unreacted MeLi which was not removed from the solid.

Part 4. $Li_2[Me_2Si(Me_3SiC_5H_3)(N\text{-}t\text{-}Bu)].¾Et_2O$ (1.44 g, 0.043 mol) was suspended in ~50 ml of ether. $ZrCl_4$ (1.0 g, 0.0043 mol) was slowly added and the reaction was allowed to stir for a few hours. The solvent was removed via vacuum and pentane was added to precipitate the LiCl. The mixture was filtered through Celite, and the filtrate was reduced in volume. The flask was placed in the freezer (−40° C.) to maximize precipitation of the product. The solid was filtered off giving 0.273 g of an off white solid. The filtrate was again reduced in volume, the precipitate filtered off to give an additional 0.345 g for a total of 0.62 g of the compound with empirical formula $Me_2Si(Me_3SiC_5H_3)(N\text{-}t\text{-}Bu)ZrCl_2$. The x-ray crystal structure of this product reveals that the compound is dimeric in nature.

Example F

Compound F: Part 1. $Me_4HC_4SiMe_2Cl$ was prepared as described in Example A for the preparation of compound A, Part 1.

Part 2. LiHNPh (4.6 g, 0.0462 mol) was dissolved in ~100 ml of thf. $Me_4HC_5SiMe_2Cl$ (10.0 g, 0.0466 mol) was slowly added. The mixture was allowed to stir overnight. The thf was removed via a vacuum. Petroleum ether and toluene were added to precipitate the LiCl, and the mixture was filtered through Celite. The solvent was removed, leaving behind a dark yellow liquid, $Me_2Si(Me_4HC_5)(NHPh)$ (10.5 g, 0.0387 mol).

Part 3. $Me_2Si(Me_4HC_5)(NHPh)$ (10.5 g, 0.0387 mol) was diluted with ~60 ml of ether. MeLi (1.4 M in ether, 56 ml, 0.0784 mol) was slowly added and the reaction was allowed to stir overnight. The resulting white solid, $Li_2[Me_2Si(Me_4C_5)(NPh).¾Et_2O$ (11.0 g), was filtered off and was washed with ether.

Part 4. $Li_2[Me_2Si(Me_4C_5)(NPh).¾Et_2O$ (2.81 g, 0.083 mol) was suspended in ~40 ml of ether. $ZrCl_4$ (1.92 g, 0.0082 mol) was slowly added, and the mixture was allowed to stir overnight. The ether was removed via a vacuum, and a mixture of petroleum ether and toluene was added to precipitate the LiCl. The mixture was filtered through Celite, the solvent mixture was removed via vacuum, and pentane was added. The mixture was placed in the freezer at −40° C. to maximize the precipitation of the product. The solid was then filtered off and washed with pentane $Me_2Si(Me_4C_5)(NPh)ZrCl_2.Et_2O$ was recovered as a pale yellow solid (1.89 g).

Example G

Compound G: The same procedure of Example F for preparing compound F was followed with the exception of the use of $HfCl_4$ in place of $ZrCl_4$ in Part 4. Thus, when $Li_2[Me_2Si(Me_4C_5)(NPh)].¾Et_2O$ (2.0 g, 0.0059 mol) and $HfCl_4$ (1.89 g, 0.0059 mol) were used, $Me_2Si(Me_4C_5)(NPh)HfCl_2.½Et_2O$ (1.70 g) was produced.

Example H

Compound H: Part 1. $MePhSiCl_2$ (14.9 g, 0.078 mol) was diluted with ~250 ml of thf. $Me_4C_5HLi$ (10.0 g, 0.078 mol) was slowly added as a solid. The reaction solution was allowed to stir overnight. The solvent was removed via a vacuum to a cold trap held at −196° C. Petroleum ether was added to precipitate out the LiCl. The mixture was filtered through Celite, and the pentane was removed from the filtrate. $MePhSi(Me_4C_5H)Cl$ (20.8 g, 0.075 mol) was isolated as a yellow viscous liquid.

Part 2. LiHN-t-Bu (4.28 g, 0.054 mol) was dissolved in ~100 ml of thf. $MePhSi(Me_4C_5H)Cl$ (15.0 g, 0.054 mol) was added drop wise. The yellow solution was allowed to stir overnight. The solvent was removed via vacuum. Petroleum ether was added to precipitate out the LiCl. The mixture was filtered through Celite, and the filtrate was evaporated down. $MePhSi(Me_4C_5H)(NH\text{-}t\text{-}Bu)$ (16.6 g, 0.053 mol) was recovered as an extremely viscous liquid.

Part 3. $MePhSi(Me_4C_5H)(NH\text{-}t\text{-}Bu)$ (16.6 g, 0.053 mol) was diluted with ~100 ml of ether. MeLi (76 ml, 0.106 mol, 1.4 M) was slowly added and the reaction mixture was allowed to stir for ~3 hours. The ether was reduced in volume, and the lithium salt was filtered off and washed with pentane producing 20.0 g of a pale yellow solid formulated as $Li_2[MePhSi(Me_4C_5)(N\text{-}t\text{-}Bu)].¾Et_2O$.

Part 4. $Li_2[MePhSi(Me_4C_5)(N\text{-}t\text{-}Bu)].¾Et_2O$ (5.0 g, 0.0131 mol) was suspended in ~100 ml of $Et_2O$. $ZrCl_4$ (3.06 g, 0.0131 mol) was slowly added. The reaction mixture was allowed to stir at room temperature for ~1.5 hours over which time the reaction mixture slightly darkened in color. The solvent was removed via vacuum and a mixture of petroleum ether and toluene was added. The mixture was filtered through Celite to remove LiCl. The filtrate was evaporated down to near dryness and filtered off. The off white solid was washed with petroleum ether. The yield of product, $MePhSi(Me_4C_5)(N\text{-}t\text{-}Bu)ZrCl_2$, was 3.82 g (0.0081 mol).

Example I

Compound I: $Li_2[MePhSi(Me_4C_5)(N\text{-}t\text{-}Bu)].¾Et_2O$ was prepared as described in Example H for the preparation of compound H, Part 3.

Part 4. $Li_2[MePhSi(Me_4C_5)(N\text{-}t\text{-}Bu)].¾Et_2O$ (5.00 g, 0.0131 mol) was suspended in ~100 ml of $Et_2O$. $HfCl_4$ (4.20 g, 0.0131 mol) was slowly added and the reaction mixture was allowed to stir overnight. The solvent was removed via vacuum and petroleum ether was added to precipitate out the LiCl. The mixture was filtered through Celite. The filtrate was evaporated down to near dryness and filtered off. The off white solid was washed with petroleum ether. MePhSi$(Me_4C_5)$(N-t-Bu)$HfCl_2$ was recovered (3.54 g, 0.0058 mole).

Example J

Compound J: MePhSi$(Me_4C_5)$(N-t-Bu)$HfMe_2$ was prepared by adding a stoichiometric amount of MeLi (1.4 M in ether) to MePhSi$(Me_4C_5)$(N-t-Bu)$HfCl_2$ suspended in ether. The white solid could be isolated in near quantitative yield.

Example K

Compound K: Part 1. $Me_4C_5SiMe_2Cl$ was prepared as described in Example A for the preparation of compound A, Part 1.

Part 2. $Me_4C_5SiMe_2Cl$ (10.0 g, 0.047 mol) was diluted with ~25 ml $Et_2O$. $LiHNC_5H_4$-p-n-Bu.⅒$Et_2O$ (7.57 g, 0.047 mol) was added slowly. The mixture was allowed to stir for ~3 hours. The solvent was removed via vacuum. Petroleum ether was added to precipitate out the LiCl, and the mixture was filtered through Celite. The solvent was removed leaving behind an orange viscous liquid, $Me_2Si(Me_4C_5H)(HNC_6H_4$-p-n-Bu) (12.7 g, 0.039 mol).

Part 3. $Me_2Si(Me_4C_5H)(HNC_6H_4$-p-n-Bu) (12.7 g, 0.039 mol) was diluted with ~50 ml of $Et_2O$. MeLi (1.4 M, 55 ml, 0.077 mol) was slowly added. The mixture was allowed to stir for ~3 hours. The product was filtered off and washed with $Et_2O$ producing $Li_2[Me_2Si(Me_4C_5)(NC_6H_4$-p-n-Bu)].¾$Et_2O$ as a white solid (13.1 g, 0.033 mol).

Part 4. $Li_2[Me_2Si(Me_4C_5)(NC_6H_4$p-n-Bu)].¾$Et_2O$ (3.45 g, 0.0087 mol) was suspended in ~50 ml of $Et_2O$. $ZrCl_4$ (2.0 g, 0.0086 mol) was slowly added and the mixture was allowed to stir overnight. The ether was removed via vacuum, and petroleum ether was added to precipitate out the LiCl. The mixture was filtered through Celite. The filtrate was evaporated to dryness to give a yellow solid which was recrystallized from pentane and identified as $Me_2Si(Me_4C_5)(NC_6H_4$-p-n-Bu)$ZrCl_2$.⅔$Et_2O$ (4.2 g).

Example L

Compound L: $Li_2[Me_2Si(Me_4C_5)(NC_6H_4$-p-n-Bu)].¾$Et_2O$ was prepared as described in Example K for the preparation of compound K, Part 3.

Part 4. $Li_2[Me_2Si(Me_4C_5)(NC_6H_4$-p-n-Bu)].¾$Et_2O$ (3.77 g, 0.0095 mol) was suspended in ~50 ml of $Et_2O$. $HfCl_4$ (3.0 g, 0.0094 mol) was slowly added as a solid and the mixture was allowed to stir overnight. The ether was removed via vacuum and petroleum ether was added to precipitate out the LiCl. The mixture was filtered through Celite. Petroleum ether was removed via a vacuum giving an off white solid which was recrystallized from pentane. The product was identified as $Me_2Si(Me_4C_5)(NC_6H_4$-p-n-Bu)$HfCl_2$ (1.54 g, 0.0027 mol).

Examples 1-34 of Polymerization

Example 1

Polymerization—Compound A

The polymerization run was performed in a 1-liter autoclave reactor equipped with a paddle stirrer, an external water jacket for temperature control, a regulated supply of dry nitrogen, ethylene, propylene, 1-butene and hexane, and a septum inlet for introduction of other solvents, transition metal compound and alumoxane solutions. The reactor was dried and degassed thoroughly prior to use. A typical run consisted of injecting 400 ml of toluene, 6 ml of 1.5 M MAO, and 0.23 mg of compound A (0.2 ml of a 11.5 mg in 10 ml of toluene solution) into the reactor. The reactor was then heated to 80° C. and the ethylene (60 psi) was introduced into the system. The polymerization reaction was limited to 30 minutes. The reaction was ceased by rapidly cooling and venting the system. The solvent was evaporated off of the polymer by a stream of nitrogen. Polyethylene was recovered (9.2 g, MW=257,200, MWD=2.275).

Example 2

Polymerization—Compound A

The polymerization was carried out as in Example 1 with the following changes: 300 ml of toluene, 3 ml of 1.5 M MAO, and 0.115 mg of compound A (0.1 ml of a 11.5 mg in 10 ml of toluene solution). Polyethylene was recovered (3.8 g, MW=359,800, MWD=2.425).

Example 3

Polymerization—Compound A

The polymerization was carried out as in Example 2 using the identical concentrations. The difference involved running the reaction at 40° C. rather than 80° C. as in the previous example. Polyethylene was recovered (2.4 g, MW=635,000, MWD=3.445).

Example 4

Polymerization—Compound A

The polymerization was carried out as in Example 1 except for the use of 300 ml of hexane in place of 400 ml of toluene. Polyethylene was recovered (5.4 g, MW=212,600, MWD=2.849).

Example 5

Polymerization—Compound A

Using the same reactor design and general procedure as in Example 1, 300 ml of toluene, 200 ml of propylene, 6.0 ml of 1.5 M MAO, and 0.46 mg of compound A (0.4 ml of a 11.5 mg in 10 ml of toluene solution) was introduced into the reactor. The reactor was heated to 80° C., the ethylene was added (60 psi), and the reaction was allowed to run for 30 minutes, followed by rapidly cooling and venting the system. After evaporation of the solvent, 13.3 g of an ethylene-propylene copolymer was recovered (MW=24,900, MWD=2.027, 73.5 SCB/1000C by IR).

Example 6

Polymerization—Compound A

The polymerization was carried out as in Example 5 except with the following changes: 200 ml of toluene and 0.92 mg of compound A (0.8 ml of a 11.5 mg in 10 ml of toluene solution). The reaction temperature was also reduced to 50° C. An ethylene-propylene copolymer was recovered (6.0 g, MW=83,100, MWD=2.370, 75.7 SCB/1000C by IR).

Example 7

Polymerization—Compound A

Using the same reactor design and general procedure as in Example 1, 150 ml of toluene, 100 ml of 1-butene, 6.0 ml of 1.5 M MAO, and 2.3 mg of compound A (2.0 ml of a 11.5 mg in 10 ml of toluene solution) were added to the reactor. The reactor was heated at 50° C., the ethylene was introduced (65 psi), and the reaction was allowed to run for 30 minutes, followed by rapidly cooling and venting the system. After evaporation of the toluene, 25.4 g of an ethylene-butene copolymer was recovered (MW=184,500, MWD=3.424, 23.5 SCB/1000C by $^{13}C$ NMR and 21.5 SCB/1000C by IR).

Example 8

Polymerization—Compound A

The polymerization was carried out as in Example 7 except with the following changes: 100 ml of toluene and 150 ml of 1-butene. An ethylene-butene copolymer was recovered (30.2 g, MW=143,500, MWD=3.097, 30.8 SCB/1000C by $^{13}C$ NMR and 26.5 SCB/1000C by IR).

Example 9

Polymerization—Compound A

The polymerization was carried out as in Example 7 except with the following changes: 200 ml of toluene, 8.0 ml of 1.0 M MAO, and 50 ml of 1-butene. An ethylene-butene copolymer was recovered (24.9 g, MW=163,200, MWD=3.290, 23.3 SCB/1000C by $^{13}C$ NMR and 18.9 SCB/1000C by IR).

Example 10

Polymerization—Compound A

The polymerization was carried out as in Example 9 except for the replacement of 200 ml of toluene with 200 ml of hexane. An ethylene-butene copolymer was recovered (19.5 g, MW=150,600, MWD=3.510, 12.1 SCB/1000 C by $^{13}C$ NMR and 12.7 SCB/1000C by IR).

Example 11

Polymerization—Compound A

The polymerization was carried out as in Example 10 except with the following changes: 150 ml of hexane, and 100 ml of 1-butene. An ethylene-butene copolymer was recovered (16.0 g, MW=116,200, MWD=3.158, 19.2 SCB/1000C by $^{13}C$ NMR and 19.4 SCB/1000C by IR).

Example 12

Polymerization—Compound A

Using the same reactor design and general procedure already described, 400 ml of toluene, 5.0 ml of 1.0 M MAO, and 0.2 ml of a preactivated compound A solution (11.5 mg of compound A dissolved in 9.0 ml of toluene and 1.0 ml of 1.0 M MAO) were added to the reactor. The reactor was heated to 80° C., the ethylene was introduced (60 psi), and the reaction was allowed to run for 30 minutes, followed by rapidly cooling and venting the system. After evaporation of the solvent, 3.4 g of polyethylene was recovered (MW=285,000, MWD=2.808).

Example 13

Polymerization—Compound A

A polymerization was carried out as in Example 12 with exception of aging the preactivated compound A solution by one day. Polyethylene was recovered (2.0 g, MW=260,700, MWD=2.738).

Example 14

Polymerization—Compound A

Using the same reactor design and general procedure already described, 400 ml of toluene, 0.25 ml of 1.0 M MAO, and 0.2 ml of a preactivated compound A solution (11.5 mg of compound A dissolved in 9.5 ml of toluene and 0.5 ml of 1.0 M MAO) were added into the reactor. The reactor was heated to 80° C., the ethylene was introduced (60 psi), and the reaction was allowed to run for 30 minutes, followed by rapidly cooling and venting the system. After evaporation of the solvent, 1.1 g of polyethylene was recovered (MW=479,600, MWD=3.130).

Example 15

Polymerization—Compound A

Using the same reactor design and general procedure already described, 400 ml of toluene and 2.0 ml of a preactivated compound A solution (11.5 mg of compound A dissolved in 9.5 ml of toluene and 0.5 ml of 1.0 M MAO) were added into the reactor. The reactor was heated to 80° C., the ethylene was introduced (60 psi), and the reaction was allowed to run for 30 minutes, followed by rapidly cooling and venting the system. After evaporation of the solvent, 1.6 g of polyethylene was recovered (MW=458,800, MWD=2.037).

Example 16

Polymerization—Compound A

Using the general procedure already described, 400 ml of toluene, 5.0 ml of 1.0 M MAO, 0.23 mg of compound A (0.2 ml of a 11.5 mg in 10 ml of toluene solution) was added to the reactor. The reactor was heated to 80° C., the ethylene introduced (400 psi), and the reaction was allowed to run for 30 minutes, followed by rapidly cooling and venting the system. After evaporation of the solvent, 19.4 g of polyethylene was recovered (MW=343,700, MWD=3.674).

Example 17

Polymerization—Compound A

The polymerization was performed in a stirred 100 ml stainless steel autoclave which was equipped to perform polymerizations at pressures up to 40,000 psi and temperatures up to 300° C. The reactor was purged with nitrogen and heated to 160° C. Compound A and alumoxane solutions were prepared in separate vials. A stock solution was prepared by dissolving 26 mg of compound A in 100 ml of toluene. The compound A solution was prepared by diluting 0.5 ml of the stock solution with 5.0 ml of toluene. The alumoxane solution consisted of 2.0 ml of a 4% MAO solution added to 5.0 ml of toluene. The compound A solution was added to the alumoxane solution, then 0.43 ml of the mixed solutions were transferred by nitrogen pressure into a constant-volume injection tube. The autoclave was pressurized with ethylene to 1784 bar and was stirred at 1500 rpm. The mixed solutions were injected into the stirred reactor with excess pressure, at which time a temperature rise of 4° C. was observed. The temperature and pressure were recorded continuously for 120 seconds, at which time the contents of the autoclave were rapidly vented into a receiving vessel. The reactor was washed with xylene to recover any additional polymer remaining within. These washings were combined with the polymer released when the autoclave was vented to yield 0.7 g of polyethylene (MW=245,500, MWD=2.257).

Example 18

Polymerization—Compound B

Using the general procedure described in Example 1, 400 ml of toluene, 5.0 ml of 1.0 M MAO and 0.278 mg compound B (0.2 ml of a 13.9 mg in 10 ml of toluene solution) was added to the reactor. The reactor was heated to 80° C. and the ethylene (60 psi) was introduced into the system. The polymerization reaction was limited to 10 minutes. The reaction was ceased by rapidly cooling and venting the system. The solvent was evaporated off the polymer by a stream of nitrogen. Polyethylene was recovered (9.6 g, MW=241,200, MWD=2.628).

Example 19

Polymerization—Compound C

Using the general procedures described in Example 1, 300 ml of toluene, 4.0 ml of 1.0 M MAO and 0.46 mg compound C (0.4 ml of a 11.5 mg in 10 ml of toluene solution) was added to the reactor. The reactor was heated to 80° C. and the ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (1.7 g, MW=278,400, MWD=2.142).

Example 20

Polymerization—Compound D

Using the general procedure described in Example 1, 400 ml of toluene, 5.0 ml of 1.0 M MAO and 0.278 mg compound D (0.2 ml of a 13.9 mg in 10 ml of toluene solution) was added to the reactor. The reactor was heated to 80° C. and the ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (1.9 g, MW=229,700, MWD=2.618).

Example 21

Polymerization—Compound E

Using the general procedure described in Example 1, 300 ml of hexane, 9.0 ml of 1.0 M MAO and 0.24 mg compound E (0.2 ml of a 12.0 mg in 10 ml of toluene solution) was added to the reactor. The reactor was heated to 80° C. and the ethylene (60 psi) was introduced into the system. The polymerization reaction was limited to 30 minutes. The reaction was ceased by rapidly cooling and venting the system. The solvent was evaporated off the polymer by a stream of nitrogen. Polyethylene was recovered (2.2 g, MW=258,200, MWD=2.348).

Example 22

Polymerization—Compound E

The polymerization was carried out as in Example 1 with the following reactor contents: 200 ml of toluene, 100 ml 1-butene, 9.0 ml of 1.0 M MAO and 2.4 mg of compound E (2.0 ml of a 12.0 mg in 10 ml of toluene solution) at 50° C. The reactor was pressurized with ethylene (65 psi), and the reaction was allowed to run for 30 minutes, followed by rapidly cooling and venting the system. After evaporation of the solvent, 1.8 g of an ethylene-butene copolymer was recovered (MW=323,600, MWD=2.463, 33.5 SCB/1000C by IR technique).

Example 23

Polymerization—Compound F

The polymerization was carried out as in Example 1 with the following reactor conditions: 400 ml of toluene, 5.0 ml of 1.0 M MAO, 0.242 mg of compound F (0.2 ml of a 12.1 mg in 10 ml of toluene solution), 80° C., 60 psi ethylene, 30 minutes. The run provided 5.3 g of polyethylene (MW=319,900, MWD=2.477).

Example 24

Polymerization—Compound F

The polymerization was carried out as in Example 1 with the following reactor conditions: 150 ml of toluene, 100 ml of 1-butene, 9.0 ml of 1.0 M MAO, 2.42 mg of compound F (2.0 ml of a 12.1 mg in 10 ml of toluene solution), 50° C., 65 psi ethylene, 30 minutes. The run provided 3.5 g of an ethylene-butene copolymer (MW=251,300, MWD=3.341, 33.28 SCB/1000C by IR technique).

Example 25

Polymerization—Compound G

The polymerization was carried out as in Example 1 with the following reactor conditions: 400 ml of toluene, 5.0 ml of 1.0 M MAO, 0.29 mg of compound G (0.2 ml of a 14.5 mg in 10 ml of toluene solution), 80° C., 60 psi ethylene, 30 minutes. The run provided 3.5 g of polyethylene (MW=237,300, MWD=2.549).

Example 26

Polymerization—Compound G

The polymerization was carried out as in Example 1 with the following reactor conditions: 150 ml of toluene, 100 ml of 1-butene, 7.0 ml of 1.0 M MAO, 2.9 mg of compound G (2.0 ml of a 14.5 mg in 10 ml of toluene solution), 50° C., 65 psi ethylene, 30 minutes. The run provided 7.0 g of an ethylene-butene copolymer (MW=425,000, MWD=2.816, 27.11 SCB/1000C by IR technique).

Example 27

Polymerization—Compound H

The polymerization was carried out as in Example 1 with the following reactor conditions: 400 ml of toluene, 5.0 ml of 1.0 M MAO, 0.266 mg of compound H (0.2 ml of a 13.3 mg in 10 ml of toluene solution), 80° C., 60 psi ethylene, 30 minutes. The run provided 11.1 g of polyethylene (MW=299,800, MWD=2.569).

Example 28

Polymerization—Compound H

The polymerization was carried out as in Example 1 with the following reactor conditions: 150 ml of toluene, 100 ml of 1-butene, 7.0 ml of 1.0 M MAO, 2.66 mg of compound H (2.0 ml of a 13.3 mg in 10 ml of toluene solution), 50° C., 65 psi ethylene, 30 minutes. The run provided 15.4 g of an ethylene-butene copolymer (MW=286,600, MWD=2.980, 45.44 SCB/1000C by IR technique).

Example 29

Polymerization—Compound I

The polymerization was carried out as in Example 1 with the following reactor conditions: 400 ml of toluene, 5.0 ml of 1.0 MAO, 0.34 mg of compound I (0.2 ml of a 17.0 mg in 10 ml of toluene solution) was added to the reactor. The reactor was heated to 80° C., the ethylene was introduced (60 psi), and the reaction was allowed to run for 30 minutes, followed by rapidly cooling and venting the system. After evaporation of the solvent, 0.9 g of polyethylene was recovered (MW=377,000, MWD=1.996).

Example 30

Polymerization—Compound J

The polymerization was carried out as in Example 1 with the following reactor conditions: 400 ml of toluene, 5.0 ml of 1.0 M MAO, 0.318 mg of compound J (0.2 ml of a 15.9 mg in 10 ml of toluene solution), 80° C., 60 psi ethylene, 30 minutes. The run provided 8.6 g of polyethylene (MW=321,000, MWD=2.803).

Example 31

Polymerization—Compound J

The polymerization was carried out as in Example 1 with the following reactor conditions: 150 ml of toluene, 100 ml of 1-butene, 7.0 ml of 1.0 M MAO, 3.18 mg of compound J (2.0 ml of a 15.9 mg in 10 ml of toluene solution), 50° C., 65 psi ethylene, 30 minutes. The run provided 11.2 g of an ethylene-butene copolymer (MW=224,800, MWD=2.512, 49.57 SCB/1000C by IR technique, 55.4 SCB/1000C by NMR technique).

Example 32

Polymerization—Compound K

The polymerization was carried out as in Example 1 with the following reactor conditions: 300 ml of toluene, 5.0 ml of 1.0 M MAO, 0.272 mg of compound K (0.2 ml of a 13.6 mg in 10 ml of toluene solution), 80° C., 60 psi ethylene, 30 minutes. The run provided 26.6 g of polyethylene (MW=187,300, MWD=2.401).

Example 33

Polymerization—Compound K

The polymerization was carried out as in Example 1 with the following reactor conditions: 150 ml of toluene, 100 ml of 1-butene, 7.0 ml of 1.0 M MAO, 2.72 mg of compound K (2.0 ml of a 13.6 mg in 10 ml of toluene solution), 50° C., 65 psi ethylene, 30 minutes. The run provided 3.9 g of an ethylene-butene copolymer (MW=207,600, MWD=2.394, 33.89 SCB/1000C by IR technique).

Example 34

Polymerization—Compound L

The polymerization was carried out as in Example 1 with the following reactor conditions: 400 ml of toluene, 5.0 ml of 1.0 M MAO, 0.322 mg of compound L (0.2 ml of a 16.1 mg in 10 ml of toluene solution), 80° C., 60 psi ethylene, 30 minutes. The run provided 15.5 g of polyethylene (MW=174,300, MWD=2.193).

Example 35

Polymerization—Compound A

The polymerization was carried out as in Example 1 with the following reactor contents: 250 ml of toluene, 150 ml of 1-hexene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 26.5 g of an ethylene-hexene copolymer was recovered (MW=222,800, MWD=3.373, 39.1 SCB/1000C by IR technique).

Example 36

Polymerization—Compound A

The polymerization was carried out as in Example 1 with the following reactor contents: 300 ml of toluene, 100 ml of 1-octene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 19.7 g of an ethylene-octene copolymer was recovered (MW=548,600, MWD=3.007, 16.5 SCB/1000C by $^{13}C$ NMR technique).

Example 37

Polymerization—Compound A

The polymerization was carried out as in Example 1 with the following reactor contents: 300 ml of toluene, 100 ml of 4-methyl-1-pentene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 15.1 g of an ethylene-4-methyl-1-pentene copolymer was recovered (MW=611,800, MWD=1.683, 1.8 mole % determined by $^{13}C$ NMR).

Example 38

Polymerization—Compound A

The polymerization was carried out as in Example 1 with the following reactor contents: 300 ml of toluene, 100 ml of a 2.2 M norbornene in toluene solution, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 12.3 g of an ethylene-norbornene copolymer was recovered (MW=812,600, MWD=1.711, 0.3 mole % determined by $^{13}C$ NMR).

Example 39

Polymerization—Compound A

The polymerization was carried out as in Example 1 with the following reactor contents: 300 ml of toluene, 100 ml of cis-1,4-hexadiene, 7.0 ml of 1.0 M MAO and 2.3 mg of compound A (2.0 ml of a 11.5 mg in 10 ml of toluene solution) at 50° C. The reactor was pressurized with ethylene (65 psi), and the reaction was allowed to run for 30 minutes, followed by rapidly cooling and venting the system. After evaporation of the solvent, 13.6 g of an ethylene-cis-1,4-hexadiene copolymer was recovered (MW=163,400, MWD=2.388, 2.2 mole % determined by $^{13}C$ NMR).

Table 2 summarizes the polymerization conditions employed and the properties obtained in the product polymers as set forth in Examples 1-34 above.

TABLE 2

| EXP. | DILUENT | | TRANSITION METAL COMPOUND (TMC) | | ALUMOXANE | | mmole MAO:TMC | | | RXN. TEMP. | RXN. TIME | YIELD | | | SCB/ 1000 C. | | CAT. ACTIVITY G. POLYMER/MMOLE |
|---|---|---|---|---|---|---|---|---|---|---|---|---|---|---|---|---|---|
| NO. | Type | ml | Type | mmole | Type | mmole | ($\times 10^3$) | MONOMER | COMONOMER | ° C. | HR. | g. | MW | MWD | NMR | IR | TMC-HOUR |
| 4 | Hexane | 300 | A | $5.588 \times 10^{-4}$ | MAO | 9 | 16.11 | ethylene- 60 psi | | 80 | 0.5 | 5.4 | 212,600 | 2.849 | | | $1.933 \times 10^4$ |
| 1 | Toluene | 400 | A | $5.588 \times 10^{-4}$ | MAO | 9 | 16.11 | ethylene- 60 psi | | 80 | 0.5 | 9.2 | 257,200 | 2.275 | | | $3.293 \times 10^4$ |
| 2 | Toluene | 300 | A | $2.794 \times 10^{-4}$ | MAO | 4.5 | 16.11 | ethylene- 60 psi | | 80 | 0.5 | 3.8 | 359,800 | 2.425 | | | $2.720 \times 10^4$ |
| 3 | Toluene | 300 | A | $2.794 \times 10^{-4}$ | MAO | 4.5 | 16.11 | ethylene- 60 psi | | 40 | 0.5 | 2.4 | 635,000 | 3.445 | | | $1.718 \times 10^4$ |
| 16 | Toluene | 400 | A | $5.588 \times 10^{-4}$ | MAO | 5 | 8.95 | ethylene- 400 psi | | 80 | 0.5 | 19.4 | 343,700 | 3.674 | | | $6.943 \times 10^4$ |
| 12 | Toluene | 400 | A[a] | $5.588 \times 10^{-4}$ | MAO | 5.02 | 8.98 | ethylene- 60 psi | | 80 | 0.5 | 3.4 | 285,000 | 2.808 | | | $1.217 \times 10^4$ |
| 13 | Toluene | 400 | A[a,b] | $5.588 \times 10^{-4}$ | MAO | 5.02 | 8.98 | ethylene- 60 psi | | 80 | 0.5 | 2.0 | 260,700 | 2.738 | | | $7.158 \times 10^3$ |
| 14 | Toluene | 400 | A[a] | $5.588 \times 10^{-4}$ | MAO | 0.26 | 0.47 | ethylene- 60 psi | | 80 | 0.5 | 1.1 | 479,600 | 3.130 | | | $3.937 \times 10^3$ |
| 15 | Toluene | 400 | A[a] | $5.588 \times 10^{-4}$ | MAO | 0.1 | 0.018 | ethylene- 60 psi | | 80 | 0.5 | 1.6 | 458,800 | 2.037 | | | $5.727 \times 10^2$ |
| 18 | Toluene | 400 | B | $5.573 \times 10^{-4}$ | MAO | 5 | 8.97 | ethylene- 60 psi | | 80 | 0.17 | 9.6 | 241,200 | 2.625 | | | $1.034 \times 10^5$ |
| 19 | Toluene | 300 | C | $1.118 \times 10^{-3}$ | MAO | 4 | 3.58 | ethylene- 60 psi | | 80 | 0.5 | 1.7 | 278,400 | 2.142 | | | $3.041 \times 10^3$ |
| 20 | Toluene | 400 | D | $5.573 \times 10^{-4}$ | MAO | 5 | 8.97 | ethylene- 60 psi | | 80 | 0.5 | 1.9 | 229,700 | 2.618 | | | $6.819 \times 10^3$ |
| 21 | Hexane | 300 | E | $5.61 \times 10^{-4}$ | MAO | 9 | 16.04 | ethylene- 60 psi | | 80 | 0.5 | 2.2 | 258,200 | 2.348 | | | $7.843 \times 10^3$ |
| 23 | Toluene | 400 | F | $4.79 \times 10^{-4}$ | MAO | 5 | 10.44 | ethylene- 60 psi | | 80 | 0.5 | 5.3 | 319,900 | 2.477 | | | $2.213 \times 10^4$ |
| 25 | Toluene | 400 | G | $5.22 \times 10^{-4}$ | MAO | 5 | 9.58 | ethylene- 60 psi | | 80 | 0.5 | 3.5 | 237,300 | 2.549 | | | $1.341 \times 10^4$ |
| 27 | Toluene | 400 | H | $5.62 \times 10^{-4}$ | MAO | 5 | 8.90 | ethylene- 60 psi | | 80 | 0.5 | 11.1 | 299,800 | 2.569 | | | $3.950 \times 10^4$ |
| 29 | Toluene | 400 | I | $5.57 \times 10^{-4}$ | MAO | 5 | 8.98 | ethylene- 60 psi | | 80 | 0.5 | 0.9 | 377,000 | 1.996 | | | $3.232 \times 10^3$ |
| 30 | Toluene | 400 | J | $5.59 \times 10^{-4}$ | MAO | 5 | 8.94 | ethylene- 60 psi | | 80 | 0.5 | 8.6 | 321,000 | 2.803 | | | $3.077 \times 10^4$ |
| 32 | Toluene | 300 | K | $5.06 \times 10^{-4}$ | MAO | 5 | 9.87 | ethylene- 60 psi | | 80 | 0.5 | 26.6 | 187,300 | 2.401 | | | $1.051 \times 10^5$ |
| 34 | Toluene | 400 | L | $5.60 \times 10^{-4}$ | MAO | 5 | 8.93 | ethylene- 60 psi | | 80 | 0.5 | 15.5 | 174,300 | 2.193 | | | $5.536 \times 10^4$ |
| 5 | Toluene | 300 | A | $1.118 \times 10^{-3}$ | MAO | 9 | 8.05 | ethylene- 60 psi | propylene- 200 ml | 80 | 0.5 | 13.3 | 24,900 | 2.027 | | 73.5 | $2.379 \times 10^4$ |
| 6 | Toluene | 200 | A | $2.235 \times 10^{-3}$ | MAO | 9 | 4.03 | ethylene- 60 psi | propylene- 200 ml | 50 | 0.5 | 6.0 | 83,100 | 2.370 | | 75.7 | $5.369 \times 10^3$ |
| 7 | Toluene | 150 | A | $5.588 \times 10^{-3}$ | MAO | 9 | 1.61 | ethylene- 65 psi | 1-butene- 100 ml | 50 | 0.5 | 25.4 | 184,500 | 3.424 | 23.5 | 21.5 | $9.091 \times 10^3$ |

TABLE 2-continued

| EXP. | DILUENT | | TRANSITION METAL COMPOUND (TMC) | | ALUMOXANE | | mmole MAO:TMC | | | RXN. TEMP. | RXN. TIME | YIELD | | | SCB/ 1000 C. | | CAT. ACTIVITY G. POLYMER/MMOLE |
|---|---|---|---|---|---|---|---|---|---|---|---|---|---|---|---|---|---|
| NO. | Type | ml | Type | mmole | Type | mmole | ($\times 10^3$) | MONOMER | COMONOMER | ° C. | HR. | g. | MW | MWD | NMR | IR | TMC-HOUR |
| 8 | Toluene | 100 | A | $5.588 \times 10^{-3}$ | MAO | 9 | 1.61 | ethylene- 65 psi | 1-butene- 150 ml | 50 | 0.5 | 30.2 | 143,400 | 3.097 | 30.8 | 26.5 | $1.081 \times 10^4$ |
| 9 | Toluene | 200 | A | $5.588 \times 10^{-3}$ | MAO | 8 | 1.43 | ethylene- 65 psi | 1-butene- 50 ml | 50 | 0.5 | 24.9 | 163,200 | 3.290 | 23.3 | 18.9 | $8.912 \times 10^3$ |
| 10 | Hexane | 200 | A | $5.588 \times 10^{-3}$ | MAO | 8 | 1.43 | ethylene- 65 psi | 1-butene- 50 ml | 50 | 0.5 | 19.5 | 150,600 | 3.510 | 12.1 | 12.7 | $6.979 \times 10^3$ |
| 11 | Hexane | 150 | A | $5.588 \times 10^{-3}$ | MAO | 8 | 1.43 | ethylene- 65 psi | 1-butene- 100 ml | 50 | 0.5 | 16.0 | 116,200 | 3.158 | 19.2 | 19.4 | $5.727 \times 10^3$ |
| 22 | Toluene | 200 | E | $5.61 \times 10^{-3}$ | MAO | 9 | 1.60 | ethylene- 65 psi | 1-butene- 100 ml | 50 | 0.5 | 1.8 | 323,600 | 2.463 | | 33.5 | $6.417 \times 10^3$ |
| 24 | Toluene | 150 | F | $4.79 \times 10^{-3}$ | MAO | 9 | 1.88 | ethylene- 65 psi | 1-butene- 100 ml | 50 | 0.5 | 3.5 | 251,300 | 3.341 | | 33.3 | $1.461 \times 10^3$ |
| 26 | Toluene | 150 | G | $5.22 \times 10^{-3}$ | MAO | 7 | 1.34 | ethylene- 65 psi | 1-butene- 100 ml | 50 | 0.5 | 7.0 | 425,000 | 2.816 | | 27.1 | $2.682 \times 10^3$ |
| 28 | Toluene | 150 | H | $5.62 \times 10^{-3}$ | MAO | 7 | 1.25 | ethylene- 65 psi | 1-butene- 100 ml | 50 | 0.5 | 15.4 | 286,600 | 2.980 | | 45.4 | $5.480 \times 10^3$ |
| 30 | Toluene | 150 | J | $5.59 \times 10^{-3}$ | MAO | 7 | 1.25 | ethylene- 65 psi | 1-butene- 100 ml | 50 | 0.5 | 11.2 | 224,800 | 2.512 | | 49.6 | $4.007 \times 10^3$ |
| 32 | Toluene | 150 | K | $5.06 \times 10^{-3}$ | MAO | 7 | 1.38 | ethylene- 65 psi | 1-butene- 100 ml | 50 | 0.5 | 3.9 | 207,600 | 2.394 | | 33.9 | $1.524 \times 10^3$ |
| 35 | Toluene | 250 | A | $5.588 \times 10^{-3}$ | MAO | 7 | 1.25 | ethylene- 65 psi | 1-hexene- 150 ml | 50 | 0.5 | 26.5 | 222,800 | 3.373 | | 39.1 | $9.485 \times 10^3$ |
| 36 | Toluene | 300 | A | $5.588 \times 10^{-3}$ | MAO | 7 | 1.25 | ethylene- 65 psi | 1-octene- 100 ml | 50 | 0.5 | 19.7 | 548,600 | 3.007 | | 16.5 | $6.979 \times 10^3$ |
| 37 | Toluene | 300 | A | $5.588 \times 10^{-3}$ | MAO | 7 | 1.25 | ethylene- 65 psi | 4-methyl- 1-pentene- 100 ml | 50 | 0.5 | 15.1 | 611,800 | 1.683 | | 1.8[c] | $5.404 \times 10^3$ |
| 38 | Toluene | 300 | A | $5.588 \times 10^{-3}$ | MAO | 7 | 1.25 | ethylene- 65 psi | norbornene- 100 ml 2.2 M | 50 | 0.5 | 12.3 | 812,600 | 1.711 | | 0.3[c] | $4.402 \times 10^3$ |
| 39 | Toluene | 300 | A | $5.588 \times 10^{-3}$ | MAO | 7 | 1.25 | ethylene- 65 psi | cis-1,4- hexadiene 100 ml | 50 | 0.5 | 13.6 | 163,400 | 2.388 | | 2.2[c] | $4.868 \times 10^3$ |

[a]Compound A was preactivated by dissolving the compound in solvent containing MAO.
[b]Preincubution of activated compound A was for one day.
[c]Mole % comonomer.

It may be seen that the requirement for the alumoxane component can be greatly diminished by premixing the catalyst with the alumoxane prior to initiation of the polymerization (see Examples 12 through 15).

By appropriate selection of (1) the Group IV B transition metal component for use in the catalyst system; (2) the type and amount of alumoxane used; (3) the polymerization diluent type and volume; and (4) reaction temperature; (5) reaction pressure, one may tailor the product polymer to the weight average molecular weight value desired while still maintaining the molecular weight distribution to a value below about 4.0.

The preferred polymerization diluents for practice of the process of the invention are aromatic diluents, such as toluene, or alkanes, such as hexane.

The resins that are prepared in accordance with this invention can be used to make a variety of products including films and fibers.

The invention has been described with reference to its preferred embodiments. Those of ordinary skill in the art may, upon reading this disclosure, appreciate changes or modifications which do not depart from the scope and spirit of the invention as described above or claimed hereafter.

The invention claimed is:

1. A compound having the general formula:

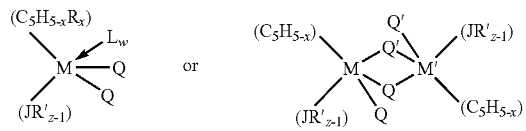

wherein M is Zr, Hf or Ti;

$(C_5H_{5-x}R_x)$ is a cyclopentadienyl ring which is substituted with from zero to five substituent groups R, x is 0, 1, 2, 3, 4 or 5 denoting the degree of substitution, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements, and halogen radicals, or $(C_5H_{5-x}R_x)$ is a cyclopentadienyl ring in which two adjacent R groups are joined forming a $C_4$-$C_{20}$ ring to give a saturated or unsaturated polycyclic cyclopentadienyl ligand;

$(JR'_{z-1})$ is a heteroatom ligand in which J is an element with a coordination number of three from Group V-A of the Periodic Table of Elements, each R' is, independently, a radical selected from a group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is, independently, selected from the group consisting of halogen, hydride or $C_1$-$C_{20}$ hydrocarbyl, provided that Q is different from $(C_5H_{5-x}R_x)$;

L is a neutral Lewis base where “w” is a number greater than 0 and up to 3;

M' has the same meaning as M; and

Q' has the same meaning as Q.

2. The compound of claim 1 wherein each Q is independently selected from the group consisting of $C_1$-$C_{20}$ hydrocarbyl.

3. The compound of claim 1 wherein each Q is independently selected from the group consisting of hydride, methyl, ethyl, propyl, butyl, amyl, hexyl, heptyl, octyl, nonyl, decyl, cetyl, phenyl, chloro, bromo, fluoro, and iodo.

4. The compound of claim 1 wherein M is Zr.

5. The compound of claim 1 wherein M is Hf.

6. A compound having the general formula

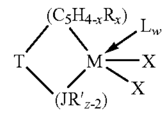

or a dimer thereof, wherein:

M is Zr, Hf or Ti;

$(C_5H_{4-x}R_x)$ is a cyclopentadienyl ring which is substituted with from zero to four substituent groups R, x is 0, 1, 2, 3, or 4 denoting the degree of substitution, provided that x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group consisting of silicon and germanium, and halogen radicals, or $(C_5H_{4-x}R_x)$ is a cyclopentadienyl ring in which two adjacent R groups are joined forming a $C_4$-$C_{20}$ ring to give a saturated or unsaturated polycyclic cyclopentadienyl ligand;

$(JR'_{z-2})$ is a heteroatom ligand in which J is an element with a coordination number of three from Group V-A or an element with a coordination number of two from Group VI-A of the Periodic Table of Elements, and R' is a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, and z is the coordination number of the element J;

X is, independently each occurrence, an anionic ligand group selected from the group consisting of halogen, hydride, or substituted or unsubstituted $C_1$ to $C_{20}$ hydrocarbyl, alkoxide, aryloxide, amide, arylamide, phosphide or arylphosphide, provided that X is different from $(C_5H_{4-x}R_x)$ or both X together may be an alkylidene or a cyclometallated hydrocarbyl;

T is a covalent bridging group containing a Group IV A or VA element; and

L is a neutral Lewis base; and w is a number from 0 to 3.

7. The compound of claim 6 wherein each X is independently selected from the group consisting of substituted and unsubstituted $C_1$ to $C_{20}$ hydrocarbyls.

8. The compound of claim 6 wherein each X is independently selected from the group consisting of hydride, methyl, ethyl, propyl, butyl, amyl, hexyl, heptyl, octyl, nonyl, decyl, cetyl, phenyl, chloro, bromo, fluoro, and iodo.

9. The compound of claim 6 wherein M is Zr.

10. The compound of claim 6 wherein M is Hf.

11. The compound of claim 6 wherein J is oxygen, phosphorus, or sulfur.

12. The compound of claim 6 wherein J is nitrogen.

13. The compound of claim 6 wherein $(C_5H_{4-x}R_x)$ is tetrahydroindenyl, fluorenyl, or octahydrofluorenyl.

14. The compound of claim 6 wherein T is methylene or ethylene.

15. The compound of claim 6 wherein T is dimethylsilyl.

16. The compound of claim 6 wherein T is diphenylsilyl.

17. The compound of claim 6 wherein X is a halide.

18. A compound having the general formula

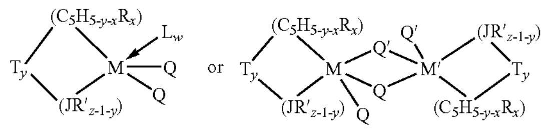

wherein M is Zr, Hf, or Ti;

M' has the same meaning as M;

$(C_5H_{5-y-x}R_x)$ is a cyclopentadienyl ring which is substituted with from zero to five substituent groups R, x is 0, 1, 2, 3, 4 or 5 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements and halogen radicals, or $(C_5H_{5-y-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-1-y})$ is a heteroatom ligand in which J is nitrogen, phosphorus, oxygen, or sulfur, and R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is 3 when J is nitrogen or phosphorus or z is 2 when J is oxygen or sulfur;

each Q is, independently, a univalent anionic ligand or two Q's together are a divalent anionic chelating ligand, provided that Q is not a substituted or unsubstituted cyclopentadienyl ring;

Q' has the same meaning as Q;

y is 0 or 1 when w is greater than 0; T is a covalent bridging group containing a Group IV-A or V-A element; and L is a neutral Lewis base, where w denotes the number 0 or 1, and when w is 0 y is 1.

19. A compound having the general formula

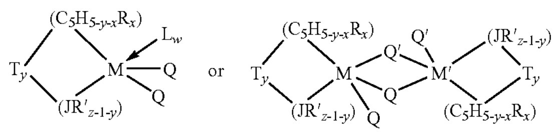

wherein M is Zr, Hf, or Ti;

M' has the same meaning as M;

$(C_5H_{5-y-x}R_x)$ is a cyclopentadienyl ring which is substituted with from zero to five substituent groups R, x is 0, 1, 2, 3, 4 or 5 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements and halogen radicals, or $(C_5H_{5-y-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-1-y})$ is a heteroatom ligand in which J is nitrogen, and R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is 3;

each Q is, independently, a univalent anionic ligand or two Q's together are a divalent anionic chelating ligand, provided that Q is not a substituted or unsubstituted cyclopentadienyl ring;

Q' has the same meaning as Q;

y is 0 or 1 when w is greater than 0; T is a covalent bridging group containing a Group IV-A or V-A element; and L is a neutral Lewis base, where w denotes the number 0 or 1, and when w is 0 y is 1.

20. A compound having the general formula

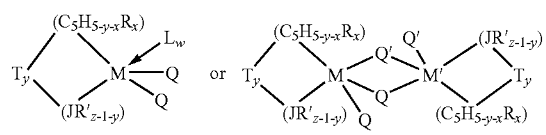

wherein M is Zr, or Hf;

M' has the same meaning as M;

$(C_5H_{5-y-x}R_x)$ is a cyclopentadienyl ring which is substituted with from zero to five substituent groups R, x is 0, 1, 2, 3, 4 or 5 denoting the degree of substitution, wherein x is 0, 1 or 3, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements and halogen radicals, or $(C_5H_{5-y-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-1-y})$ is a heteroatom ligand in which J is an element with a coordination number of three from Group V-A or an element with a coordination number of two from Group VI-A of the Periodic Table of Elements, and each R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is, independently, a univalent anionic ligand or two Q's together are a divalent anionic chelating ligand, provided that Q is not a substituted or unsubstituted cyclopentadienyl ring;

Q' has the same meaning as Q;

y is 0 or 1 when w is greater than 0; T is a covalent bridging group containing a Group IV-A or V-A element; and L is a neutral Lewis base, where w denotes the number 0 or 1, and when w is 0 y is 1.

21. A compound having the general formula

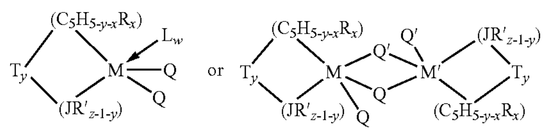

wherein M is Ti, Zr, or Hf;

M' has the same meaning as M;

$(C_5H_{5-y-x}R_x)$ is a cyclopentadienyl ring which is substituted with from zero to five substituent groups R, x is 0, 1, 2, 3, 4 or 5 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements and halogen radicals, or $(C_5H_{5-y-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-1-y})$ is a heteroatom ligand in which J is an element with a coordination number of three from Group V-A or an element with a coordination number of two from Group VI-A of the Periodic Table of Elements, and each R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is independently selected from the group consisting of halogen, hydride or a substituted or unsubstituted $C_1$-$C_{20}$ hydrocarbyl, alkoxide, aryloxide, amide, arylamide, phosphide, or arylphosphide, provided that Q is not a substituted or unsubstituted cyclopentadienyl ring, or both Q together are an alkylidene or a cyclometallated hydrocarbyl;

Q' has the same meaning as Q;

y is 0 or 1 when w is greater than 0; T is a covalent bridging group containing a Group IV-A or V-A element; and L is a neutral Lewis base, where w denotes the number 0 or 1, and when w is 0 y is 1.

22. A compound having the general formula

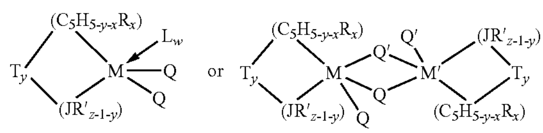

wherein M is Zr, Hf, or Ti;

M' has the same meaning as M;

$(C_5H_{5-y-x}R_x)$ is a cyclopentadienyl ring which is substituted with from zero to five substituent groups R, x is 0, 1, 2, 3, 4 or 5 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements or $(C_5H_{5-y-x}R_x)$ is a cyclopentadienyl ring in which two adjacent R groups are joined forming a $C_4$-$C_{20}$ ring to give a saturated or unsaturated polycyclic cyclopentadienyl ligand;

$(JR'_{z-1-y})$ is a heteroatom ligand in which J is an element with a coordination number of three from Group V-A or an element with a coordination number of two from Group VI-A of the Periodic Table of Elements, and each R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen atom, and z is the coordination number of the element J;

each Q is, independently, a univalent anionic ligand or two Q's together are a divalent anionic chelating ligand, provided that Q is not a substituted or unsubstituted cyclopentadienyl ring;

Q' has the same meaning as Q;

y is 0 or 1 when w is greater than 0; y is 1 when w is 0; T is a covalent bridging group containing a Group IV-A or V-A element and L is a Lewis base; where w denotes a number from 0 to 3.

23. The compound of claim 22 wherein each Q is a halogen or $C_1$ to $C_{20}$ hydrocarbyl radical.

24. A compound represented by general formula

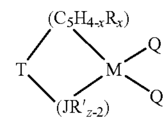

wherein M is Zr, Hf, or Ti;

$(C_5H_{4-x}R_x)$ is a cyclopentadienyl ring which is substituted with from zero to four substituent groups R, x is 0, 1, 2, 3, or 4 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, and halogen radicals, or $(C_5H_{4-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-2})$ is a heteroatom ligand in which J is an element with a coordination number of three from Group V-A, and R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is 3;

each Q is, independently, a univalent anionic ligand group or two Q's together are a divalent anionic chelating ligand, provided that Q is not a substituted or unsubstituted cyclopentadienyl ring; and T is a covalent bridging group containing a Group IV-A or V-A element.

25. A compound having the general formula:

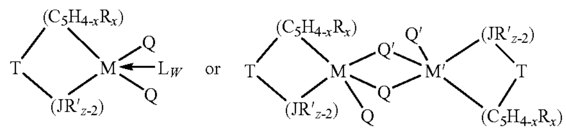

wherein M is Zr, Hf, or Ti;

M' has the same meaning as M;

$(C_5H_{4-x}R_x)$ is a cyclopentadienyl ring which is substituted with from zero to four substituent groups R, x is 0, 1, 2, 3, or 4 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, and halogen radicals, or $(C_5H_{4-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-2})$ is a heteroatom ligand in which J is an element with a coordination number of three from Group V-A or an element with a coordination number of two from Group VI-A of the Periodic Table of Elements, and R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is, independently, a univalent anionic ligand or two Q's together are a divalent anionic chelating ligand, provided that Q is not a substituted or unsubstituted cyclopentadienyl ring;

Q' has the same meaning as Q;

T is a covalent bridging group selected from the group consisting of dialkyl, alkylaryl, or diaryl substituted silicon or germanium radicals; and L is a neutral Lewis base where w denotes the number 0 or 1.

26. A compound having the general formula:

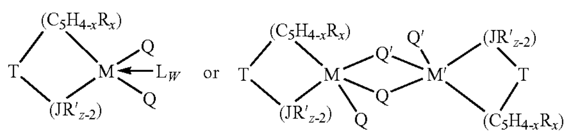

wherein M is Zr, Hf, or Ti;

M' has the same meaning as M;

$(C_5H_{4-x}R_x)$ is a cyclopentadienyl ring which is substituted with from zero to four substituent groups R, x is 0, 1, 2, 3, or 4 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, and halogen radicals, or $(C_5H_{4-x}R_x)$ is a cyclopentadienyl ring in which two adjacent R substituents are joined forming a $C_4$-$C_{20}$ ring to give a saturated or unsaturated polycyclic cyclopentadienyl ligand;

$(JR'_{z-2})$ is a heteroatom ligand in which J is an element with a coordination number of three from Group V-A or an element with a coordination number of two from Group VI-A of the Periodic Table of Elements, and R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is, independently, a univalent anionic ligand or two Q's together are a divalent anionic chelating ligand, provided that Q is not a substituted or unsubstituted cyclopentadienyl ring;

Q' has the same meaning as Q;

T is a covalent bridging group selected from the group consisting of methylene and ethylene radicals; and L is a neutral Lewis base where w denotes the number 0 or 1.

27. The compound of claim 24 wherein Q is independently selected from the group consisting of halogen, hydride and $C_1$ to $C_{20}$ hydrocarbyl.

28. The compound of claim 25 wherein Q is independently selected from the group consisting of halogen, hydride or $C_1$ to $C_{20}$ hydrocarbyl.

29. The compound of claim 26 wherein Q is independently selected from the group consisting of halogen, hydride or $C_1$ to $C_{20}$ hydrocarbyl.

30. The compound of claim 24 wherein each Q is independently selected from the group consisting of hydride, methyl, ethyl, propyl, butyl, amyl, hexyl, heptyl, octyl, nonyl, decyl, cetyl, phenyl, chloro, bromo, and iodo.

31. The compound of claim 25 wherein each Q is independently selected from the group consisting of hydride, methyl, ethyl, propyl, butyl, amyl, hexyl, heptyl, octyl, nonyl, decyl, cetyl, phenyl, chloro, bromo, and iodo.

32. The compound of claim 26 wherein each Q is independently selected from the group consisting of hydride, methyl, ethyl, propyl, butyl, amyl, hexyl, heptyl, octyl, nonyl, decyl, cetyl, phenyl, chloro, bromo, and iodo.

33. A process for the polymerization of one or more alpha olefins comprising conducting the polymerization in the presence of a catalyst system comprising (A) the compound of claim 6 and (B) an alumoxane.

34. The process of claim 33 wherein the mole ratio of Al:M is from 10:1 to 20,000:1.

35. The process of claim 33 wherein the one or more alpha olefins is ethylene.

36. The process of claim 33 wherein the one or more alpha olefins is propylene.

37. The process of claim 33 wherein the one or more alpha olefins is (1) ethylene in combination with an alpha olefin having 3 to 20 carbon atoms, (2) propylene in combination with ethylene and/or C4 or higher alpha-olefins and diolefins, or (3) butene in combination with ethylene and/or C4 or higher alpha-olefins and diolefins.

38. A process for the polymerization of one or more alpha olefins comprising conducting the polymerization in the presence of a catalyst system comprising:

(A) a Group IV B transition metal component of the formula:

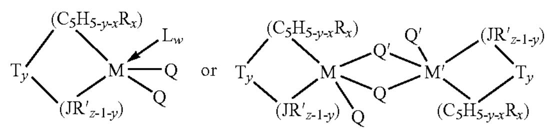

wherein M is Zr, Hf or Ti;

M' has the same meaning as M;

$(C_5H_{5-y-x}R_x)$ is a cyclopentadienyl ring which is substituted with from zero to five groups R, x is 0, 1, 2, 3, 4 or 5 denoting the degree of substitution, wherein x is 0, 1, 2, 3 or 4 when M is Ti and x is 0, 1 or 3 when M is Hf or Zr, and each R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements, and halogen radicals, or $(C_5H_{5-y-x}R_x)$ is a cyclopentadienyl ring in which two adjacent R-groups are joined forming a $C_4$-$C_{20}$ ring to give a saturated or unsaturated polycyclic ligand;

$(JR'_{z-1-y})$ is a heteroatom ligand in which J is an element with a coordination number of three from Group V-A or an element with a coordination number of two from Group VI-A of the Periodic Table of Elements, and each R' is, independently, a radical selected from the group consisting of $C_1$-$C_{20}$ hydrocarbyl radicals, substituted $C_1$-$C_{20}$ hydrocarbyl radicals where one or more hydrogen atoms is replaced by a halogen atom, and z is the coordination number of the element J;

each Q is, independently, any univalent anionic ligand or two Q's together are a divalent anionic chelating ligand, provided that Q is different from $(C_5H_{5-y-x}R_x)$;

Q' has the same meaning as Q;

y is 0 or 1 when w is greater than 0; y is 1 when w is 0; T is a covalent bridging group containing a Group IV-A or V-A element; and L is a Lewis base where w denotes, a number 0 to 3;

(B) an alumoxane, wherein the olefin is styrene.

39. A process for the polymerization of one or more alpha olefins comprising conducting the polymerization in the presence of a catalyst system comprising:

(A) a Group IV B transition metal component of the formula:

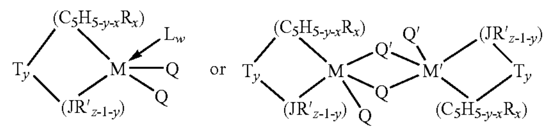

wherein M is Zr, Hf or Ti;

M' has the same meaning as M;

$(C_5H_{5-y-x}R_x)$ is a cyclopentadienyl ring which is substituted with from zero to four substituent groups R, x is 0, 1, 2, 3 or 4 denoting the degree of substitution, wherein x is 0, 1, 2, 3 or 4 when M is Ti and x is 0, 1 or 3 when M is Hf or Zr, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements, and halogen radicals, or $(C_5H_{5-y-x}R_x)$ is a cyclopentadienyl ring in which two adjacent R-groups are joined forming a $C_4$-$C_{20}$ ring to give a saturated or unsaturated polycyclic ligand;

$(JR'_{z-1-y})$ is a heteroatom ligand in which J is an element with a coordination number of three from group V-A or an element with a coordination number of two from Group VI-A of the Periodic Table of Elements, and each R' is a radical selected from the group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is, independently, a univalent anionic ligand or two Q's together are a divalent anionic chelating ligand, provided that Q is different from $(C_5H_{5-x}R_x)$;

Q' has the same meaning as Q;

y is 1;

T is a covalent bridging group containing a Group IV-A or V-A element; and

L is a neutral Lewis base where w denotes the number 0 or 1;

(B) an alumoxane.

40. The process of claim 39 wherein each Q is, independently, a substituted or unsubstituted $C_1$-$C_{20}$ hydrocarbyl, phosphide or arylphosphide radical, provided that Q is not a substituted or unsubstituted cyclopentadienyl ring, or both Q together are an alkylidene or a cyclometallated hydrocarbyl.

41. The process of claim 39 wherein the heteroatom ligand group J element is nitrogen, phosphorous, oxygen or sulfur.

42. The process of claim 39 wherein Q is substituted or unsubstituted C1 to C20 hydrocarbyl radical.

43. The process of claim 39 wherein the heteroatom ligand group J element is nitrogen.

44. The process of claim 39 wherein the mole ratio of Al:M is from 10:1 to 20,000:1.

45. The process of claim 39 wherein the alpha olefin is (1) ethylene, (2) propylene, (3) ethylene in combination with an alpha olefin having 3 to 20 carbon atoms, (4) propylene in combination with ethylene and/or C4 or higher alpha-olefins and diolefins, or (5) butene in combination with ethylene and/or C4 or higher alpha-olefins and diolefins.

46. The process of claim 39 wherein both Q are selected from the group consisting of: methyl, ethyl, propyl, butyl, amyl, isoamyl, hexyl, isobutyl, heptyl, octyl, nonyl, decyl, cetyl, 2-ethylhexyl, and phenyl.

47. The process of claim 39 wherein both Q are methyl.

48. The process of claim 39 wherein both Q are selected from the group consisting of: diphenylphosphide, dicyclohexylphosphide, dimethylphosphide, methylidene, ethylidene and propylidene.

49. The process of claim 39 wherein the alpha olefin is ethylene.

50. The process of claim 39 wherein the alpha olefin is propylene.

51. A process for the polymerization of one or more alpha olefins comprising conducting the polymerization in the presence of a catalyst system comprising:

(A) a Group IV B transition metal component of the formula:

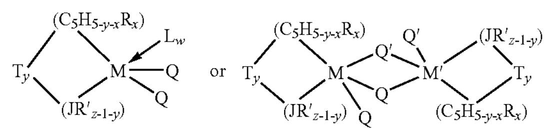

wherein M is Zr, Hf, or Ti;

M' has the same meaning as M;

$(C_5H_{5-y-x}R_x)$ is a cyclopentadienyl ring which is substituted with from zero to four substituent groups R, x is 0, 1, 2, 3 or 4 denoting the degree of substitution, wherein x is 0, 1, 2, 3 or 4 when M is Ti and x is 0, 1 or 3 when M is Hf or Zr, and each substituent group R is, independently, a radical selected from the group consisting of straight alkyl radicals having 1 to 20 carbon atoms, branched alkyl radicals having 1 to 20 carbon atoms, trimethylsilyl, triethylsilyl, ethyldimethylsilyl, methyldiethylsilyl, and triphenylgermyl, or $(C_5H_{4-x}R_x)$ is a cyclopentadienyl ring in which two adjacent R substituents are joined forming a $C_4$-$C_{20}$ ring to give a saturated or unsaturated polycyclic cyclopentadienyl ligand;

(JR'z-1-y) is a heteroatom ligand selected from the group consisting of t-butylamido, phenylamido, p-n-butylphenylamido, perfluorophenylamido, benzylamido, t-butylphosphido, ethylphosphido, phenylphosphido, and cyclohexylphosphido, and z is 3;

each Q selected is from the group consisting of hydride, methyl, ethyl, n-propyl, isopropyl, n-butyl, isobutyl, amyl, isoamyl, hexyl, heptyl, octyl, nonyl, decyl, cetyl, phenyl, chloro, bromo, fluoro, iodo, methoxy, ethoxy, propoxy, butoxy, phenoxy, dimethylamido, diethylamido, methylethylamido, di-t-butylamido, diphenylamido, diphenylphosphido, dicyclohexylphosphido, and dimethylphosphido;

Q' has the same meaning as Q;

y is 1;

T is selected from the group consisting of dialkyl, alkylaryl, or diaryl substituted silicon or germanium radicals, unsubstituted methylene and ethylene radicals;

L is a neutral Lewis base where w denotes the number 0 or 1; and (B) an alumoxane.

52. The process of claim 51 wherein T is selected from the group consisting of dimethylsilyl, diethylsilyl, di-n-propylsilyl, diisopropylsilyl, di-n-butylsilyl, di-t-butylsilyl, di-n-hexylsilyl, methylphenylsilyl, ethylmethylsilyl, diphenylsilyl, n-hexylmethylsilyl, cyclopentamethylenesilyl, cyclotetramethylenesilyl, cyclotrimethylenesilyl, dimethylgermyl, and diethylgermyl.

53. The process of claim 51 wherein the process is solution process.

54. A compound having the general formula:

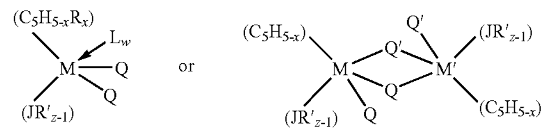

wherein M is Zr, Hf or Ti;

$(C_5H_{5-x}R_x)$ is a cyclopentadienyl ring which is substituted with from zero to five substituent groups R, x is 0, 1, 2, 3, 4 or 5 denoting the degree of substitution, and each substituent group R is, independently, a radical selected from the group consisting of $C_1$-$C_{20}$ hydrocarbyl radicals, substituted $C_1$-$C_{20}$ hydrocarbyl radicals wherein one or more hydrogen atoms is replaced by a halogen atom, $C_1$-$C_{20}$ hydrocarbyl-substituted metalloid radicals wherein the metalloid is selected from the group IV A of the Periodic Table of Elements, and halogen radicals, or $(C_5H_{5-x}R_x)$ is a cyclopentadienyl ring in which two adjacent R groups are joined forming a $C_4$-$C_{20}$ ring to give a saturated or unsaturated polycyclic cyclopentadienyl ligand;

$(JR'_{z-1})$ is a heteroatom ligand in which J is an element with a coordination number of three from Group V-A or an element with a coordination number of two from Group VI-A of the Periodic Table of Elements, each R' is, independently, a radical selected from a group consisting of $C_1$-$C_{20}$ hydrocarbyl radicals, substituted $C_1$-$C_{20}$ hydrocarbyl radicals where one or more hydrogen atoms is replaced by a halogen radical, and z is the coordination number of the element J;

each Q is, independently, selected from the group consisting of halogen, hydride and $C_1$-$C_{20}$ hydrocarbyl, provided that Q is different from $(C_5H_{5-x}R_x)$;

L is a neutral Lewis base where "w" is a number greater than 0 and up to 3;

M' has the same meaning as M; and

Q' has the same meaning as Q.

55. The compound of claim 6 wherein J is oxygen.

56. The compound of claim 6 wherein X is selected from the group consisting of halogen, hydride and $C_1$-$C_{20}$ hydrocarbyl.

* * * * *